(12) United States Patent
Wilson et al.

(10) Patent No.: US 8,512,932 B2
(45) Date of Patent: *Aug. 20, 2013

(54) METHOD FOR IMPROVING THE PHARMACEUTIC PROPERTIES OF MICROPARTICLES COMPRISING DIKETOPIPERAZINE AND AN ACTIVE AGENT

(75) Inventors: Bryan R. Wilson, Bedford, NY (US); Marshall Grant, Newtown, CT (US)

(73) Assignee: MannKind Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/239,696

(22) Filed: Sep. 22, 2011

(65) Prior Publication Data

US 2012/0010133 A1   Jan. 12, 2012

Related U.S. Application Data

(63) Continuation of application No. 11/678,046, filed on Feb. 22, 2007, now Pat. No. 8,039,431.

(60) Provisional application No. 60/776,605, filed on Feb. 22, 2006.

(51) Int. Cl.
*A61K 38/28* (2006.01)
*G03G 13/08* (2006.01)

(52) U.S. Cl.
USPC .......... 430/120.1; 106/740; 514/5.9; 530/303

(58) Field of Classification Search
None
See application file for complete search history.

(56) References Cited

U.S. PATENT DOCUMENTS

| | | | |
|---|---|---|---|
| 5,352,461 A | 10/1994 | Feldstein et al. | |
| 5,503,852 A | 4/1996 | Steiner et al. | |
| 5,532,461 A | 7/1996 | Crummenauer et al. | |
| 5,976,574 A | 11/1999 | Gordon | |
| 5,985,248 A | 11/1999 | Gordon et al. | |
| 6,001,336 A | 12/1999 | Gordon | |
| 6,051,256 A | 4/2000 | Platz et al. | |
| 6,071,497 A | 6/2000 | Steiner et al. | |
| 6,077,543 A | 6/2000 | Gordon et al. | |
| 6,331,318 B1 | 12/2001 | Milstein | |
| 6,365,190 B1 | 4/2002 | Gordon et al. | |
| 6,372,258 B1 | 4/2002 | Platz et al. | |
| 6,395,300 B1 | 5/2002 | Straub et al. | |
| 6,395,774 B1 | 5/2002 | Milstein | |
| 6,423,344 B1 | 7/2002 | Platz et al. | |
| 6,428,771 B1 | 8/2002 | Steiner et al. | |
| 6,440,463 B1 | 8/2002 | Feldstein et al. | |
| 6,444,226 B1 * | 9/2002 | Steiner et al. ................. | 424/489 |
| 6,479,049 B1 | 11/2002 | Platz et al. | |
| 6,509,006 B1 | 1/2003 | Platz et al. | |
| 6,569,406 B2 | 5/2003 | Stevenson et al. | |
| 6,572,893 B2 | 6/2003 | Gordon et al. | |
| 6,582,728 B1 | 6/2003 | Platz et al. | |
| 6,635,283 B2 | 10/2003 | Edwards et al. | |
| 6,652,885 B2 | 11/2003 | Steiner et al. | |
| 6,663,898 B2 | 12/2003 | Milstein | |
| 6,838,076 B2 | 1/2005 | Patton et al. | |
| 6,847,595 B2 | 1/2005 | Tanaka | |
| 6,884,435 B1 | 4/2005 | O'Hagan et al. | |
| 6,896,906 B2 | 5/2005 | Hastedt et al. | |
| 7,820,676 B2 * | 10/2010 | Leone-Bay et al. ...... | 514/255.02 |
| 7,919,119 B2 | 4/2011 | Straub et al. | |
| 8,039,431 B2 * | 10/2011 | Wilson et al. .................. | 514/5.9 |
| 2006/0040953 A1 | 2/2006 | Leone-Bay et al. | |
| 2006/0041133 A1 | 2/2006 | Stevenson et al. | |
| 2007/0059373 A1 | 3/2007 | Oberg | |
| 2007/0059374 A1 | 3/2007 | Hokenson et al. | |
| 2012/0207913 A1 | 8/2012 | Smyth | |

FOREIGN PATENT DOCUMENTS

| | | |
|---|---|---|
| EP | 1 060 741 | 12/2000 |
| WO | 91/16038 | 10/1991 |
| WO | 93/18754 | 9/1993 |
| WO | 95/00127 | 1/1995 |
| WO | 96/13250 | 5/1996 |
| WO | 02/058735 | 8/2002 |
| WO | 02/098348 | 12/2002 |
| WO | 2005/020964 | 3/2005 |
| WO | 2006/023943 | 3/2006 |
| WO | 2006/023943 A1 | 3/2006 |
| WO | 2006/023944 | 3/2006 |
| WO | 2007/033316 A2 | 3/2007 |
| WO | 2007/121411 A2 | 10/2007 |

OTHER PUBLICATIONS

Wilson, et al., at , [Retrieved from]: http://www.aapsj.org/abstracts/AM_2004/AAPS2004-002724.PDF, 1 page, 2004.*
Retrieved from website: http://groups.molbiosci.northwestern.edu/holmgren/Glossary/Definitions/Def-P/placebo.html, 1 page, Retrieved on Mar. 12, 2013.*
Katchalski E et al. "Synthesis of lysine anhydride" J Amer Chem Soc 68:879-880, 1946.
Kopple KD et al. "A convenient synthesis of 2,5-piperazinediones" J Org Chem 33:862-864, 1968.
Lian H et al. "A self-complementary, self-assembling microsphere system: application for intravenous delivery of the antiepileptic and neuroprotectant compound felbamate" J. Pharm Sci 89:867-875, 2000.
Pfutzner et al. "Technosphere/Insulin—A New Approach for Effective Delivery of Human Insulin Via the Pulmonary Route." Diabetes Technology & Therapeutics, vol. 4, p. 589-594, 2002.
International Preliminary Report on Patentability for International Application No. PCT/US2006/035822 dated Mar. 18, 2008.
European Office Action for EP Application No. 06 803 583.1 dated Dec. 22, 2011.
CN Office Action cited in Application No. 200880122670.3 mailed on Nov. 23, 2011.
Johnson, Keith A., "Preparation of peptide and protein powders for inhalation," Advanced Drug Delivery Reviews 1997; 26: 3-15.
Seville, P.C. et al., "Preparation of dry powder dispersions for non-viral gene delivery by freeze-drying and spray drying," J Gene Medicine 2002; 4: 428-437.

* cited by examiner

*Primary Examiner* — Satyanarayana R Gudibande
(74) *Attorney, Agent, or Firm* — K&L Gates LLP; Louis C. Cullman; Hal Gibson

(57) ABSTRACT

Methods are provided for drying a particle. Specifically, there is provided a spray-dried diketopiperazine-insulin particle formulation having improved aerodynamic performance and in which the active agent is more stabile and efficiently delivered as compared to that of the lyophilized diketopiperazine-insulin formulation. The dry powders have utility as pharmaceutical formulations for pulmonary delivery.

27 Claims, 17 Drawing Sheets

Spray dried at 0.4 bar

Spray dried at 0.6 bar

Spray dried at 0.7 bar

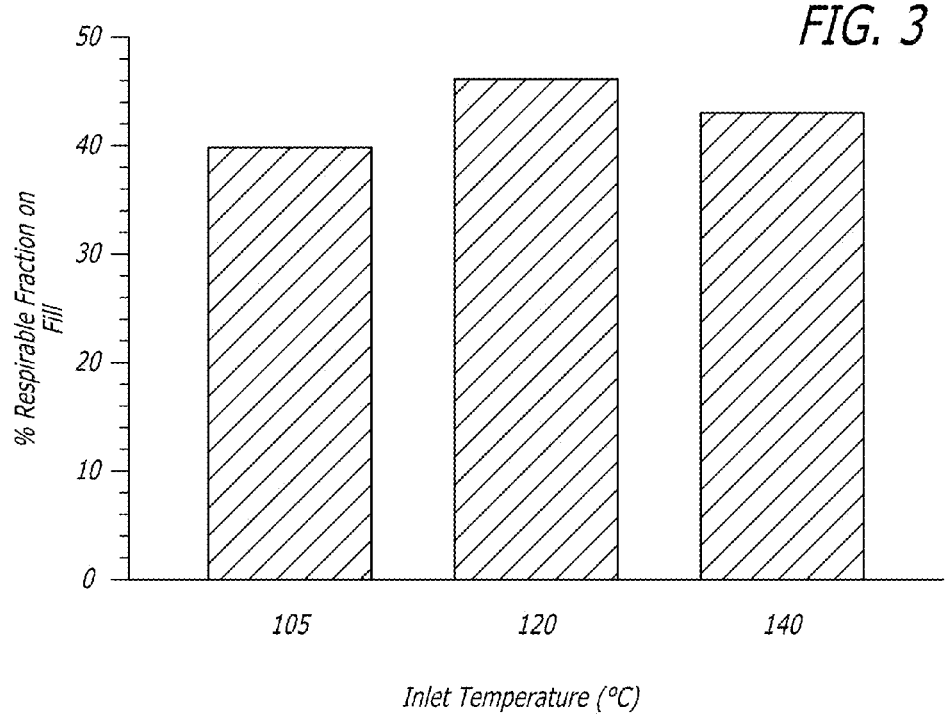

Spray dried at 105°C, 11 gram scale

Spray dried at 120°C, 11 gram scale

Spray dried at 120°C, 45 gram scale

Spray dried at 140°C, 11 gram scale

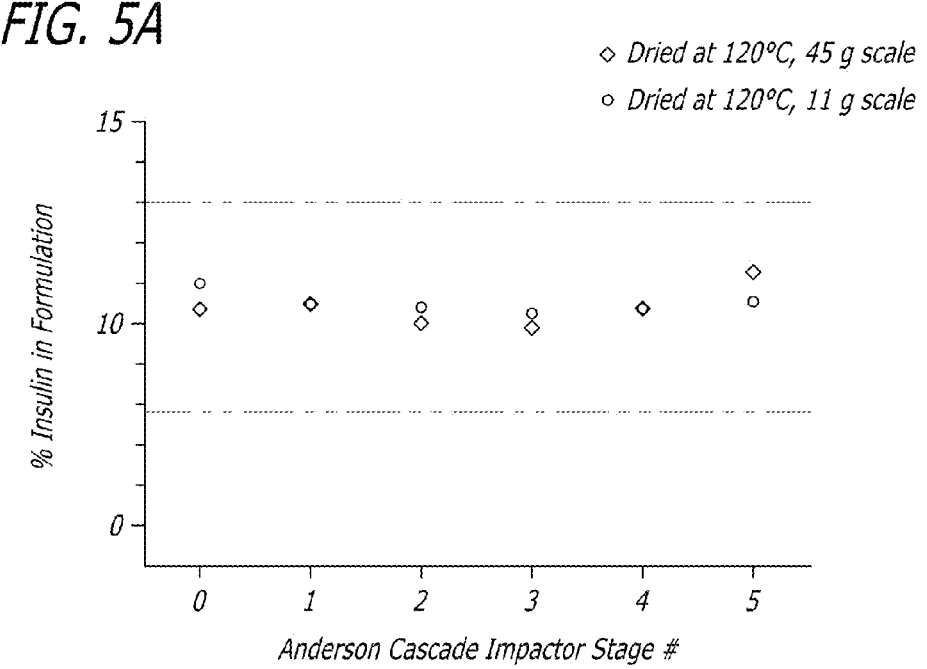

*FIG. 5B*          *FIG. 5C*
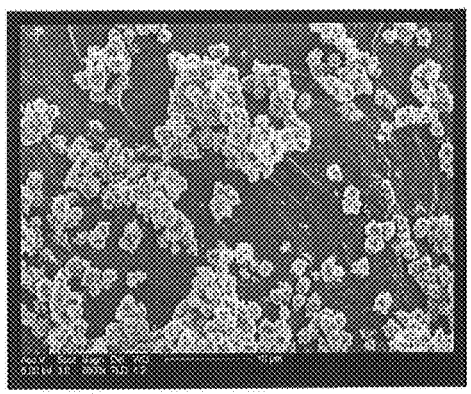
Lyophilized Formulation- 2,500 x
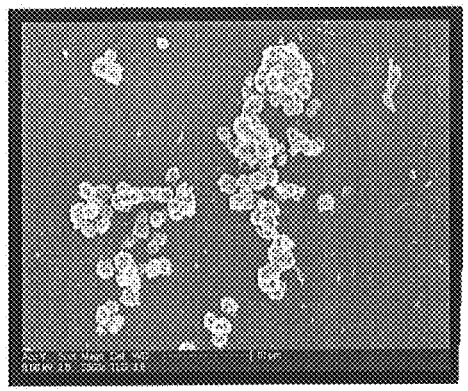
Spray Dried Formulation- 2,500 x
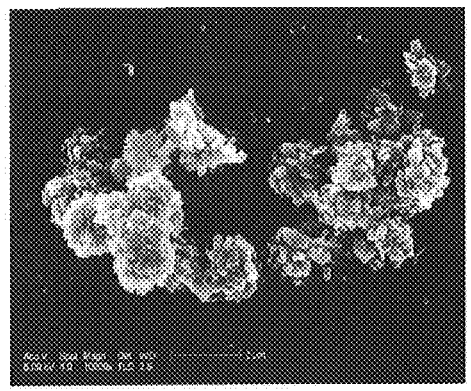
Lyophilized Formulation- 10,000 x
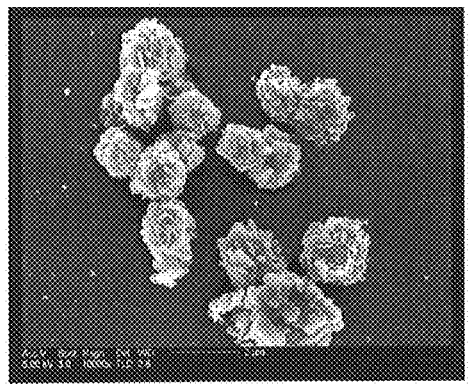
Spray Dried Formulation- 10,000 x
*FIG. 5D*          *FIG. 5E*

FIG. 6A

*% Respirable Fraction on Fill* vs *Atomization Pressure (bar)*

FIG. 6B

*% RF on Fill* vs *Temperature (°C)*

Spray dried at 110°C, 0.7bar

Spray dried at 110°C, 0.9bar

Spray dried at 110°C, 1.1bar

Spray dried at 120°C, 0.7bar

Spray dried at 120°C, 0.9bar

Spray dried at 120°C, 1.1bar

METHOD FOR IMPROVING THE PHARMACEUTIC PROPERTIES OF MICROPARTICLES COMPRISING DIKETOPIPERAZINE AND AN ACTIVE AGENT

CROSS REFERENCE TO RELATED APPLICATIONS

The present application is a continuation of U.S. Pat. No. 8,039,431 filed Feb. 22, 2007, which claims priority under 35 U.S.C. 119(e) to U.S. Provisional Application No. 60/776,605 filed Feb. 22, 2006, the contents of each of which is incorporated by reference herein in its entirety.

BACKGROUND OF THE INVENTION

1. Field of the Invention

The invention relates to the field of dry powder pharmaceuticals. The invention discloses methods of obtaining particles with improved aerodynamic performance or in which the active agent is more stable and efficiently delivered. More particularly, the present invention concerns methods for drying, particularly spray drying diketopiperazine-insulin (DKP-insulin) particles. The dry powders of the invention have utility as pharmaceutical formulations for pulmonary delivery.

2. Description of the Related Art

A number of different methodologies are employed in the art for preparing particles as a dry powder composition. These methodologies include, for example, lyophilization, evaporation, phase separation, and spray drying (see PCT Patent Application: WO 91/16038). In the manufacture of dry powder pharmaceuticals some methods start with the components in solution and form the particles of the powder by removing solvent. Other methods form particles in a separate, earlier step, such as by precipitation, and can result in a particle in suspension, which must then be dried. Methods such as lyophilization and evaporation are often used particularly for drying or removing a solvent from particles in suspension, whereas spray drying has more typically been used for particle formation from solution. For example, see U.S. Pat. Nos. 5,976,574; 5,985,248; 6,001,336; 6,051,256; 6,077,543; 6,365,190; 6,372,258; 6,423,344; 6,479,049; 6,509,006; 6,569,406; 6,572,893; 6,582,728; 6,838,076; and 6,896,906.

Lyophilization, or freeze drying, involves a process in which solvent, typically water, is removed from a product after it is frozen and placed under a vacuum, allowing the ice to change directly from solid to vapor without passing through a liquid phase. The process consists of three separate, unique, and interdependent processes; freezing, primary drying (sublimation), and secondary drying (desorption). During spray drying, a (generally aqueous) solution is introduced via a nozzle (e.g., a two fluid nozzle), spinning disc, or an equivalent device into a hot gas stream. Passage through the nozzle atomizes the solution into fine droplets. The heat energy supplied by the gas stream causes the evaporation of water or other solvents, thereby producing fine particles.

Drug delivery using substituted diketopiperazine microparticles has been described in U.S. Pat. Nos. 5,352,461; 5,503,852; 6,331,318; 6,395,774 and 6,663,898. Pulmonary delivery of diketopiperazine microparticles as dry powders is described in U.S. Pat. Nos. 5,503,852; 6,428,771; 6,444,226 and 6,652,885. Various methods for forming and loading diketopiperazine particles for drug delivery are disclosed in U.S. Pat. No. 6,444,226, U.S. patent application Ser. Nos. 11/532,063 and 11/532,065 both filed on Sep. 14, 2006, and U.S. Provisional Patent Application Ser. No. 60/717,524, filed on Sep. 14, 2005. Each of these documents is incorporated herein by reference for all they contain regarding diketopiperazines, diketopiperazine microparticles and their use in drug delivery. Dry powders made according to these teachings work well for pulmonary delivery; however there remains room for improvement of various pharmaceutic properties. The present invention serves to overcome the need in the art for obtaining improved particles having superior aerodynamics and providing more efficient delivery and greater stability of the active agent.

SUMMARY OF THE INVENTION

The present invention is directed to methods of obtaining an improved particle and/or an improved dry powder. The particles and powders contemplated by the present invention are comprised of a diketopiperazine derivative combined with an active agent. In particular embodiments of the present invention, the particle is a diketopiperazine-insulin particle formulation having improved stability, aerodynamic properties, and pharmacodynamic properties when dried by the process of spray drying as compared to that of freeze drying. In other embodiments, there is provided a spray-dried diketopiperazine-insulin particle formulation or dry powder.

In a particular embodiment of the present invention, the particle comprising a diketopiperazine is prepared and provided in a suspension, typically an aqueous suspension, to which a solution of the active agent is added. Active agents of the present invention may include one or more of the following: insulin, calcitonin, parathyroid hormone 1-34, or other bioactive fragment of parathyroid hormone, octreotide, leuprolide, and RSV peptide, felbamate, cannabinoid antagonists and/or agonists, muscarinic antagonists and/or agonists, heparin, low molecular weight heparin, cromolyn, sildenafil, vardenafil, tadalafil growth hormone, zidovudine (AZT), didanosine (DDI), granulocyte-colony stimulating factor (GCSF), lamotrigine, chorionic gonadotropin releasing factor, luteinizing release hormone, β-galactosidase, GLP-1, exendins 1-4, ghrelin, and fragments thereof, but are not limited to such. In another embodiment, the active agent is a peptide or protein such as insulin or an analogue thereof.

In a particular embodiment, the active agent is insulin or an analogue thereof.

The present invention discloses methods of obtaining particles with improved aerodynamic performance and in which the active agent is more stable and efficiently delivered. More particularly, the present invention concerns methods for drying, particularly spray drying, diketopiperazine-insulin particles. The dry powders have utility as pharmaceutical formulations for pulmonary delivery. In other embodiments, the diketopiperazine-insulin dry powders may be utilized for nasal delivery.

Thus, in particular embodiments the present invention provides a method of preparing a dry powder medicament with an improved pharmaceutic property, comprising the steps of: (a) providing a solution of a diketopiperazine; (b) providing a solution of an active agent; (c) forming particles; and (d) combining the diketopiperazine and the active agent; and thereafter (e) removing solvent by spray drying to obtain a dry powder, wherein the dry powder has an improved pharmaceutic property as compared to a dry powder obtained by removing solvent by lyophilization.

In another embodiment, the improved pharmaceutic property is selected from the group consisting of improved stability of the active agent, increased density of the dry powder, and improved aerodynamic performance of the dry powder.

In still yet another embodiment, an improved aerodynamic performance of the dry powder is measured by the percentage of particles in the respirable range (respirable fraction) delivered from the inhaler. The respirable fraction, as contemplated in the present invention, may be greater than about 40% or greater than about 50%, or greater than about 60%, but is not limited to such.

In other embodiments of the present invention, it is contemplated that the insulin content of the microparticles is within the range of about 3% to about 50% by weight of the dry powder formulation. In other instances, the insulin concentration is within the range of about 7% to about 25% by weight. In preferred embodiments insulin content is about 19.0, 19.1, 19.2 19.3, 19.4, 19.5, 19.6, 19.7, 19.8, or 19.9% by weight. In another preferred embodiment, insulin concentration is at about 11% by weight. In still other preferred embodiments the insulin content is about 10, 12, 13, 14, 15, 16, 17, or 18% by weight. In various embodiments, about is defined as ±0.1, 0.2, 0.5, 1, or 2%, so long as the uncertainty does not exceed 10% of the insulin content.

In still yet another embodiment, there is provided in the present invention a diketopiperazine having the formula 2,5-diketo-3,6-di(4-X-aminobutyl)piperazine, wherein X is selected from the group consisting of succinyl, glutaryl, maleyl, and fumaryl. In a preferred embodiment, the diketopiperazine is fumaryl diketopiperazine.

In yet another particular embodiment of the present invention there is provided a dry powder prepared according to the method of preparing a dry powder medicament with an improved pharmaceutic property, comprising the steps of: (a) providing a solution of a diketopiperazine; (b) providing a solution of an active agent; (c) forming particles; and (d) combining the diketopiperazine and the active agent; and thereafter (e) removing solvent by spray drying to obtain a dry powder, wherein the dry powder has an improved pharmaceutic property as compared to a dry powder obtained by removing solvent by lyophilization. In a further embodiment, the dry powder comprises an active agent such as insulin or an analogue thereof, but is not limited to such.

In still yet another particular embodiment, the present invention provides a method for delivering insulin to a patient in need thereof, comprising administering to the patient an effective amount of the dry powder.

The present invention also provides a dry powder having an improved pharmaceutic property wherein the improved property is improved delivery of the active agent whereby greater glucose disposal is achieved.

In still yet another particular embodiment of the present invention, there is provided a method of preparing a dry powder medicament with an improved pharmaceutic property, comprising: (a) providing a diketopiperazine in solution; (b) a step for forming particles comprising the diketopiperazine; (c) and removing solvent by spray drying to obtain a dry powder, wherein the dry powder has an improved pharmaceutic property as compared to a dry powder obtained by removing solvent by lyophilization. A further step comprising loading the particle with an active agent prior to the solvent removal step is also provided.

Another particular embodiment of the present invention provides a method of optimizing the aerodynamic performance of a diketopiperazine dry powder comprising the steps of: (a) precipitating a diketopiperazine from solution under a controlled temperature to form particles; (b) selecting a drying method based on said temperature; and (c) drying the particles. A further step comprising loading the particles with an active agent is also contemplated.

In particular embodiments the inlet temperature during spray drying is 105° C., 110° C., 120° C., 130° C., 140° C., or a range bounded by any pair of these values. In other particular embodiments the atomization pressure is 0.4, 0.5, 0.6, 0.7, 0.8, 0.9, 1.0, 1.1 bar or a range bounded by any pair of these values. In further particular embodiments the spray rate is 4.4, 7.6, 12.2 g/min, or a range bounded by any pair of these values. In still another particular embodiment of the present invention the outlet temperature is 75° C.

In a further embodiment, the diketopiperazine is fumaryl diketopiperazine, wherein the controlled temperature is between about 15° C. to about 18° C. and the selected drying method is spray drying. In other embodiments the controlled temperature is about 17° C. In still other embodiments the controlled temperature is less than or equal to about 13° C. or greater than or equal to about 19° C.

In a further particular embodiments there is contemplated a particle containing about 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0% or greater, insulin by weight. In a particular embodiment of the present invention there is provided a particle containing about 11.4% insulin by weight. In another particular embodiment there is contemplated a particle comprising up to 50% insulin by weight.

The active agent such as, but not limited to, insulin, comprised in a solution or suspension, is mixed with a suspension of a diketopiperazine wherein, the solution or suspension is in a suitable solvent for both the active agent and the diketopiperazine In some embodiments, the present invention provides a method of obtaining a dry powder comprising a diketopiperazine and an active agent such as insulin, having improved pharmaceutic properties by precipitating the particles from a solution at a controlled temperature between about 15° C. to about 18° C. In other embodiments the controlled temperature is about 17° C. In still other embodiments the controlled temperature is less than or equal to about 13° C. or greater than or equal to about 19° C.

In other embodiments of the present invention the term 'Cartridge Fill Weight' as used herein refers to the quantity of drug product contained in a cartridge for an inhaler, typically 5-10 mg or more. In other embodiments the cartridge fill weight can vary from about 2.5 to 15 mg, 10 to 20 mg, or 5 to 30 mg.

In further embodiments the bulk or tapped density of the powder dried by spray drying is increased compared to a similar powder dried by lyophilization. In one such embodiment the density is greater by a factor of about 2 (1.7-2.3). Particular further embodiments include those limited to values disclosed in the examples or a range bounded by any pair of those values. In various embodiments the bulk density of the spray-dried powder is 0.150-0.200 g/cc. Particular embodiments include those limited to values disclosed in the examples or a range bounded by any pair of those values. In various embodiments the tapped density of the spray-dried powder is 0.250-0.300 g/cc. Particular embodiments include those limited to values disclosed in the examples or a range bounded by any pair of those values.

In yet another embodiment of the present invention the term 'Cartridge Emptying' as used herein refers to the percentage (%) of powder that is discharged from the inhaler upon activation (or discharge). This value is typically obtained by weighing the cartridge before and after discharge. Particular embodiments include those limited to values disclosed in the examples or a range bounded by any pair of those values.

In still yet another embodiment of the present invention the term 'Respirable Fraction (RF)' as used herein refers to the percentage (%) of particles in the respirable range (0.5-5.8 μm). The 'Respirable Fraction (RF) delivered' refers to the percentage of active ingredient able to reach the airways of the lung where the pharmaceutical effect is exerted. Particular embodiments include those limited to values disclosed in the examples or a range bounded by any pair of those values.

In another embodiment of the present invention the term 'Respirable Fraction Based on Fill' '% RF Based on Fill', '% RF on Fill' or '% RF/fill') as used herein refers to the percentage (%) of powder in the respirable range normalized by the quantity of powder in the inhaler. Particular embodiments include those limited to values disclosed in the examples or a range bounded by any pair of those values.

BRIEF DESCRIPTION OF THE DRAWINGS

The following drawings form part of the present application and are included to further demonstrate certain aspects of the present invention. The invention may be better understood by reference to one or more of these drawings in combination with the detailed description of specific embodiments presented herein.

FIG. 2B depicts a corresponding decrease in the formation of A-21, the primary degradation product of insulin under these conditions. FIGS. 2C-2E demonstrate that the primary particles exhibit a decreased tendency to aggregate as the atomization pressure is increased from 0.4 bar (FIG. 2C) to 0.6 bar (FIG. 2D) to 0.7 bar (FIG. 2E). The measurements were obtained using laser diffraction.

FIG. 3. Demonstration of the effect of temperature on the aerodynamics of the diketopiperazine-insulin formulations. The outlet temperature was held at 75° C. and the atomization pressure was held at 0.6 bar. The % RF on Fill (percent respirable fraction on a cartridge fill) remained relatively consistent over the temperature range.

FIG. 4A depicts the percent loss of insulin. FIG. 4B depicts formation of A-21, the most prevalent degradation product. FIG. 4C-4F depicts a trend towards increased aggregation of primary particles (as shown by the particles size distribution obtained from laser diffraction) as the inlet temperature is increased from 105° C. (FIG. 4C) to 120° C. (FIGS. 4D and 4E) to 140° C. (FIG. 4F).

FIGS. 5A-5E. Insulin distribution and particle morphology. FIG. 5A shows that insulin is evenly distributed throughout the formulation independent of particle size. FIGS. 5B-5E shows that the morphology of the spray-dried particles (FIGS. 5C and 5E) and lyophilized particles (FIGS. 5B and 5D) is the same.

FIGS. 6A-6B. Improvement in particle aerodynamics and insulin stability. FIG. 6A shows that % RF on Fill increases with atomization pressure at 0.7, 0.9 and 1.1 bar respectively. FIG. 6B shows that % RF on Fill does not change with inlet temperature at 110° C., 120° C. and 130° C. respectively.

FIG. 7A depicts measurement of the accelerated stability as percentage of insulin loss for powders spray dried at a pressure of 0.7 bar and inlet temperatures of 110° C., 120° C., and 130° C. respectively. FIG. 7B depicts measurement of the accelerated stability as percentage of insulin loss for powders spray dried at a pressure of 1.1 bar and inlet temperatures of 110° C., 120° C., and 130° C. respectively. FIGS. 7C-7K depicts minimal aggregation of primary particles (as shown by the particles size distribution obtained from laser diffraction) as the atomization pressure was varied from 0.7-1.1 bar and the inlet temperature was varied from 110° C., 120° C., and 130° C. respectively.

DETAILED DESCRIPTION OF THE EMBODIMENTS OF THE INVENTION

Figure 1:
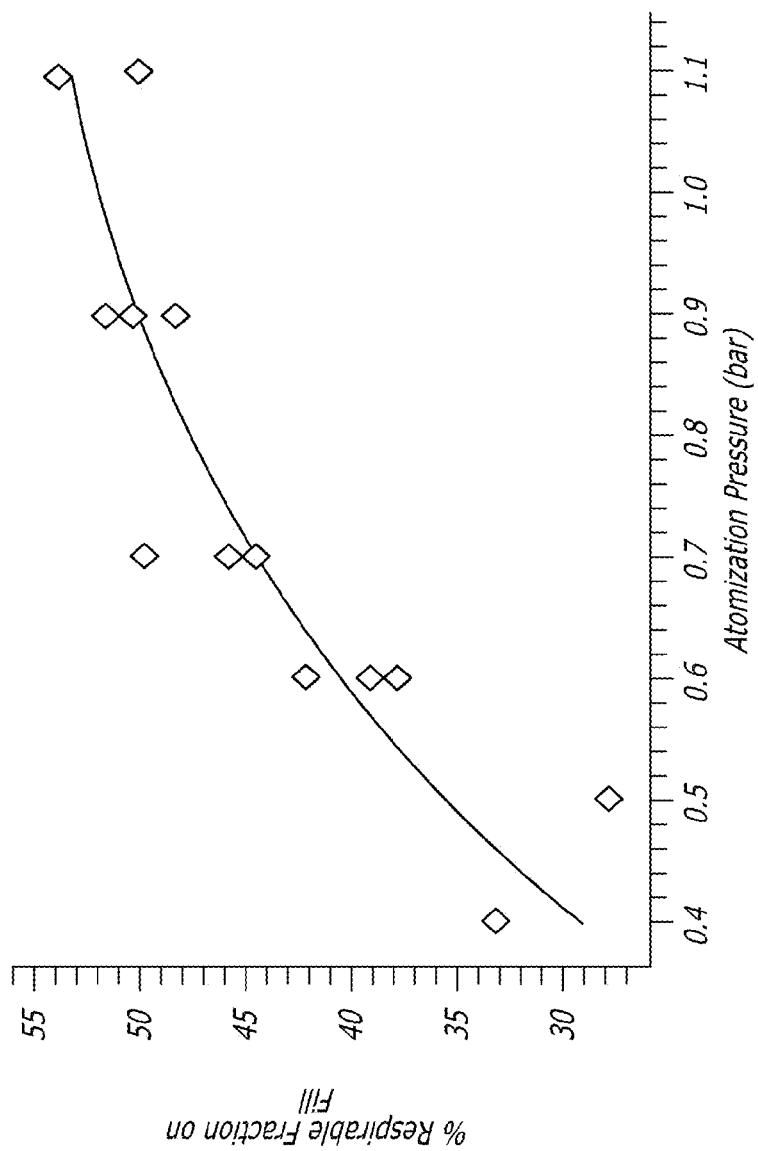
FIG. 1. Demonstration that increased atomization pressure had a positive effect on the aerodynamics of the diketopiperazine-insulin formulations. The inlet temperature ranged from 110° C. to 140° C. and the outlet temperature was held constant at 75° C.

The success of any pharmaceutic particle depends not only on its efficacy in treating a disease or condition, but also having superior pharmaceutic properties over other known therapeutics. Desirable pharmaceutic properties sought in a dry powder particle include improved aerodynamics, pharmacodynamics and stability. However, producing particles with such properties is an ongoing challenge in the art. One approach to achieving this aim in the art, lies in the methodology used to manufacture particles.

Thus, the present invention provides the novel and unexpected discovery that the pharmaceutic properties of the dry powder can be generally improved by using spray drying in preference to lyophilization to remove solvent from the particles.

The present invention serves to overcome the shortcomings in the art by providing particles of a diketopiperazine (DKP) combined with an active agent that are loaded and/or dried by a process to provide a dry powder having improved pharmaceutic properties. In particular embodiments, the present invention provides a particle, comprising a diketopiperazine combined with insulin, dried by spray drying. The invention further provides a spray-dried powder that demonstrates improved stability, aerodynamics or greater density, while maintaining at least similar pharmacodynamics as compared to the freeze-dried powder previously disclosed (see U.S. Pat. No. 6,444,226 entitled "Purification and Stabilization of Peptide and Protein Pharmaceutical Agents" and U.S. Patent Application Ser. Nos. 60/717,524, filed on Sep. 14, 2005 and Ser. No. 11/532,063 filed Sep. 14, 2006, both entitled "Method of Drug Formulation Based on Increasing the Affinity of Active Agents for Crystalline Microparticle Surfaces"), each incorporated herein by reference for all they contain regarding diketopiperazine microparticle compositions.

Diketopiperazine particles for drug delivery can be formed and loaded with active agent by a variety of methods. Diketopiperazine solutions can be mixed with solutions or suspensions of an active agent and then precipitated to form particles comprising the active agent. Alternatively the DKP can be precipitated to form particles and subsequently mixed with a solution of the active agent. Association between the particle and the active agent can occur spontaneously, be driven by solvent removal, a specific step can be included prior to drying, or any combinations of these mechanisms applied to promote the association. Further variations along these lines will be apparent to one of skill in the art.

In one particular protocol the precipitated diketopiperazine particles are washed, a solution of insulin is added, the mixture frozen by dropwise addition to liquid nitrogen and the resulting frozen droplets (pellets) lyophilized (freeze-dried) to obtain a diketopiperazine-insulin dry powder. In other embodiments, the mixture can be dispersed into the liquid nitrogen by other means, for example, by spraying. In other protocols the precipitated diketopiperazine particles of the invention are washed, a solution of insulin added, the pH of the solution adjusted to promote insulin adsorption onto the particles, and solvent removed either by spray drying or freeze drying to obtain a diketopiperazine-insulin dry powder. Previously, lyophilization had been used for solvent removal and it had been expected that the use of spray drying for this purpose would produce similar results. As disclosed herein, it was surprisingly discovered that spray-dried dry powder possessed improved pharmaceutic characteristics. In particular the spray-dried powder had an improved respirable fraction (% RF), the insulin contained in the particles had greater stability against degradation and the particles had a greater density allowing higher doses to be loaded into any particular volume. Upon pulmonary administration, at least comparable amounts of insulin were delivered into the bloodstream as evidenced by at least comparable reductions in blood glucose. The performance of the spray-dried powders was superior to the lyophilized powders whether or not the preparation of the lyophilized samples included a pH-adjustment to promote association of the drug with the particle.

In a further refinement of the methodology, the temperature of the solution from which the DKP was precipitated was controlled. Surprisingly, FDKP particles precipitated from solutions at temperatures ≦about 13° C. or about ≧19° C., dry powders with greater % RF were obtained using lyophilization for solvent removal. For FDKP particles precipitated from solutions at temperatures at about 17° C., dry powders with greater % RF were obtained using spray drying for solvent removal. In the remaining portions of the tested range, aerodynamic performance was similar with either drying method. Thus aerodynamic performance of DKP particles can be optimized by selecting a solvent removal procedure on the basis of the temperature of the solution from which the particles are precipitated. The dry powders obtained were characterized for aerodynamic properties (% RF, cartridge emptying, % RF/fill, mass median aerodynamic diameter [MMAD], geometric standard deviation [GSD]) and physicochemical properties (insulin content [% load], yield, density) as described in examples provided herein.

Surprisingly, the density of the spray-dried particles was roughly twice that of freeze-dried particles. This can be advantageous in providing higher doses. Dry powder inhalers generally impose a limit on the volume of powder, and thus the dosage of active agent, that can be delivered in a single operation. A powder of higher density, but at least similar respirable fraction, allows larger doses to be administered in a single operation, rather than requiring more operations per dose, formulations with higher % loading of active agent, or alternate inhaler or inhaler cartridge designs to accommodate various volumes of powder. Any of these alternatives entail greater development and/or production costs and also introduce issues of product complexity. Product complexity and requirements for multiple operations per dose additionally create issues with product acceptance and patient compliance. Thus this unexpected increase in powder density offers multiple advantages for the use of spray-dried powders as pharmaceutical products.

1. Preparing Preformed Particles by Spray Drying

Spray drying, as employed in the present invention, is a thermal processing method used to load and/or dry particles in a suspension in a liquid medium (solvent). As disclosed in the examples herein, a suspension of diketopiperazine particles and an insulin solution are mixed. Some or all of the insulin molecules then bind to the diketopiperazine particles. In various embodiments the diketopiperazine-insulin particles are then loaded and/or dried by spray drying and a dry powder is obtained. In an alternative embodiment, the active agent is added to a diketopiperazine solution prior to precipitation of the particles.

During spray drying, the aqueous mixture of diketopiperazine particles or diketopiperazine-insulin particles, are introduced via a nozzle (e.g., a two fluid nozzle or high pressure nozzle), spinning disc, or an equivalent device into a heated gas stream. Prior to being passed through the heated gas stream, the solution or suspension is atomized into fine droplets. The heat energy supplied by the gas stream causes the evaporation of water and other solvents in which the particles are suspended, thereby producing dry powder compositions.

In obtaining a dry powder comprising a diketopiperazine combined with insulin, as in embodiments of the present invention, the inventors found that the spray drying method generally provided particles with superior pharmaceutic properties compared to similar particles obtained by freeze drying. In obtaining the particles, the inventors took into consideration a number of parameters. These parameters included temperature, atomization pressure, solids content of the suspensions, percent of insulin loss, formation of A-21, aggregation of particles, and aerodynamic and biological performance.

The inlet temperature is the temperature of the gas stream leaving its source. The outlet temperature is a measure of the final temperature of the powder formulation and an indication of the utilization of the energy in the inlet air for drying and is a function of the inlet temperature and the heat load required to dry the product, along with other factors. The outlet temperature is selected based upon the lability of the macromolecule being treated.

The diketopiperazine/active agent mixture may be a suspension. The solvent, generally water, rapidly evaporates from the droplets producing a fine dry powder.

Spray drying is performed under conditions that result in a powder of homogeneous constitution having a particle size that is respirable, with low moisture content and other characteristics that allow for aerosolization. Preferably the particle size of the resulting powder is such that more than about 98% of the particles (by mass) have a diameter of about 10 μm or less with about 90% of the particles (by mass) have a diameter less than 5 μm. Alternatively, about 95% of the particles (by mass) have a diameter of less than 10 μm with about 80% of the particles (by mass) have a diameter of less than 5 μm. In certain embodiments, the dry powder has a mean particle size of 1 to 5 μm in diameter. The preceding embodiments relate especially to use of the powder in pulmonary delivery. Mean particle size can effect where in the respiratory tract particles are deposited and can also effect their bulk handling properties. For example nasal deposition is favored for particles with mean diameters greater than 20 μm. In other embodiments, the powder may be used to form tablets, packaged in capsules, or resuspended for oral administration or injection. Thus in various embodiments, the dry powder may comprise particles having a mean particle size of greater than about 10 μm, 20 μm, 30 μm, 40 μm, 50 μm, 60 μm, 70 μm, 80 μm, 90 μm, 100 μm. In another embodiment, the dry powder may comprise particles having a mean particle size of about 100 μm to about 500 μm. In other embodiments, the dry powder may comprise particles having a mean particle size of less than about 1 mm.

Suspensions of the present invention, comprising an active agent and a diketopiperazine may be spray-dried in conventional spray drying equipment such as the PHARMASD™ PSD-1 Spray Dryer or the SD-Micro™ Spray Dryer, as are well known in the art and obtainable from a commercial supplier (Niro Inc., Columbia, Md.), thereby resulting in a dry powder comprised of such particles. It is noted that other conventional spray drying equipment may be used.

In conducting spray drying experimentation, methods such as rotary atomization, pressure atomization, and two-fluid atomization (for example, co-current two-fluid nozzle and/or fountain two-fluid nozzle) may be employed. Devices used in spray drying methodology are well known to one of ordinary skill in the art.

Although no special restrictions are placed on the nozzle of the atomizer used in the process of spraying, for a nozzle which can produce a spray-dry composition with a grain diameter suitable for nasal pharyngeal or pulmonary administration it is recommended in the art to use nozzles such as those in the following examples. For example, nozzle types "1A," "1," "2A," "2," "3" and the like, (manufactured by Yamato Chemical Co.), or the SB Series SprayDry® Nozzles (manufactured by Spraying Systems Co.), can be used with the spray-dryer. In addition, disks type "MC-50," "MC-65" or "MC-85," (manufactured by Okawara Kakoki Co.), can be used as rotary disks of the spray-drier atomizer.

In other embodiments, the inlet gas temperature used to dry the sprayed material is such that it does not cause heat deactivation of the active agent. The range of inlet temperatures may vary between about 50° C. to about 200° C., preferably between about 110° C. and 160° C. With well-stabilized agents, the inlet temperature can exceed 200° C. The temperature of the outlet gas used to dry the sprayed material may vary between about 35° C. and about 100° C., preferably between 55° C. and 85° C. In other embodiments, the outlet temperature may be preferably at 75° C. In another embodiment of the present invention, the inlet and outlet temperatures may be held at 120° C. and 75° C. respectively.

As disclosed above and elsewhere herein, terminology useful and applicable to the methods and compositions of the present invention are as follows:

The term "powder" means a composition that consists of fine solid particles that are capable of being dispersed in an inhalation device and inhaled by a subject. In preferred embodiments the particles reach the lungs or alveoli. Such a powder is said to be "respirable." Preferably the average particle size is less than about 10 microns (μm) in diameter with a relatively uniform spheroidal shape distribution. More preferably the diameter is less than about 7.5 μm and most preferably less than about 5.0 μm. Usually, the particle size distribution is between about 0.1 μm and about 8 μm in diameter, particularly about 0.3 μm to about 5 μm.

The term "dry" means that the powder composition is not suspended or dissolved in a propellant, carrier, or other liquid. It is not meant to imply a complete absence of water. The composition can have a moisture content such that the particles are readily dispersible in an inhalation device to form an aerosol. This moisture content is generally below about 10% by weight (% w) water, usually below about 5% weight and preferably less than about 3% weight.

The term "effective amount" is the amount that is needed to provide a desired response in the subject to be treated. The precise dosage will vary according to a variety of factors including, but not limited to, the age and size of the subject, the disease and the treatment being effected. The "effective amount" will also be determined based on the anticipated pharmacodynamic response or bioavailability.

2. Diketopiperazines

Diketopiperazines can be formed into particles that incorporate an active agent or particles onto which an active agent can be adsorbed. Diketopiperazines of the present invention include but are not limited 3,6-di(fumaryl-4 aminobutyl)-2,5-diketopiperazine also known as (E)-3,6-bis[4-(N-carboxyl-2-propenyl)amidobutyl]-2,5-diketopiperazine (which may also be referred to as fumaryl diketopiperazine or FDKP).

Other diketopiperazines that are contemplated in the present invention include 3,6-di(4-aminobutyl)-2,5-diketopiperazine; 3,6-di(succinyl-4-aminobutyl)-2,5-diketopiperazine (succinyl diketopiperazine or SDKP); 3,6-di(maleyl-4-aminobutyl)-2,5-diketopiperazine; 3,6-di(citraconyl-4-aminobutyl)-2-5-diketopiperazine; 3,6-di(glutaryl-4-aminobutyl)-2,5-diketopiperazine; 3,6-di(malonyl-4-aminobutyl)-2,5-diketopiperazine; 3,6-di(oxalyl-4-aminobutyl)-2,5-diketopiperazine and derivatives therefrom.

In brevity, diketopiperazines can be formed by cyclodimerization of amino acid ester derivatives, as described by Katchalski, et al., (J. Amer. Chem. Soc. 68:879-80; 1946), by cyclization of dipeptide ester derivatives, or by thermal dehydration of amino acid derivatives in high-boiling solvents, as described by Kopple, et al., (J. Org. Chem. 33(2):862-64; 1968), the teachings of which are incorporated herein.

Methods for synthesis and preparation of diketopiperazines are well known to one of ordinary skill in the art and are disclosed in U.S. Pat. Nos. 5,352,461; 5,503,852; 6,071,497; 6,331,318; and 6,428,771; and U.S. patent application Ser. No. 11/208,087 each of which is incorporated herein by reference for all they teach regarding diketopiperazines. U.S. Pat. No. 6,444,226, herein incorporated by reference for all it contains regarding diketopiperazine microparticles, describes preparing and providing microparticles of diketopiperazines in aqueous suspension to which a solution of active agent is added. This patent further describes a method of removing a liquid medium by lyophilization to yield microparticles comprising an active agent. See also U.S. Pat. No. 6,440,463 and U.S. patent application Ser. Nos. 11/532,063 and 11/532,025 both filed on Sep. 14, 2006, and U.S. Provisional Patent Application Ser. No. 60/717,524, filed on Sep. 14, 2005; each of which is incorporated herein by reference for all they teach regarding diketopiperazine microparticles.

In one embodiment, active agent is encapsulated within microparticles by dissolving a diketopiperazine with acidic side chains in bicarbonate or other basic solution, adding the active agent in solution or suspension, and then precipitating the microparticle by adding acid, such as 1 M citric acid. In another embodiment, active agent is encapsulated within microparticles by dissolving a diketopiperazine with basic side chains in an acidic solution, such as 1 M citric acid, adding the active agent in solution or suspension, and then precipitating the microparticle by adding bicarbonate or another basic solution. In still another embodiment, active agent is encapsulated within microparticles by dissolving a diketopiperazine with both acidic and basic side chains in an acidic or basic solution, adding the active agent in solution or suspension to be encapsulated, then precipitating the microparticle by neutralizing the solution. In an alternative embodiment, microparticles of diketopiperazine are prepared and provided in a suspension, typically an aqueous suspension, to which a solution of the active agent then is added.

It is further contemplated that the diketopiperazine-insulin particle formulations of the present invention can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets, or capsules.

3. Active Agents

Embodiments of the present invention employ particles combining an active agent with a diketopiperazine. The term 'active agent' is referred to herein as the therapeutic agent, or molecule (such as protein or peptide or biological molecule), to be encapsulated, associated, joined, complexed or entrapped in or to the diketopiperazine of the present invention. Generally speaking, any form of an active agent can be combined with a diketopiperazine of the present invention. Active agents, as contemplated in the present invention, may or may not be charged.

Active agents contemplated for use in the compositions and methods described herein may include any polymer or large organic molecules, most preferably peptides and proteins. Examples include synthetic organic compounds, proteins and peptides, polysaccharides and other sugars, lipids, and nucleic acid sequences, having therapeutic, prophylactic, or diagnostic activities. Active agents may also include small molecules and vitamins. An active agent of the present invention may also be a vasoactive agent, a neuroactive agent, a hormone, an agent regulating metabolism, weight, or blood glucose levels, an anticoagulant, an immunomodulating agent, a cytotoxic agent, an antibiotic, an antiviral, an antisense molecule, or an antibody.

Examples of specific exemplary active agents have been listed above. In particular embodiments of the invention the active agent is insulin or an analogue thereof. Analogues with faster, slower, shorter, or longer action profiles are known in the art. Such analogues include those with altered amino acid sequences and those that have been covalently modified with other moieties, such as polyethylene glycol, or additional amino acids, such as in a fusion protein. Ultimately any molecule with a substantial portion of a wild type insulin molecule and physiologically relevant insulin activity is comprehended by this term.

Proteins as contemplated by the present invention are defined as consisting of 100 amino acid residues or more; in addition, peptides contemplated by the invention are less than 100 amino acid residues.

4. Stabilizing Agents Contemplated in the Present Invention

In further embodiments, there is contemplated by the present invention the use of stabilizing agents that may be contained in a suspension or solution comprising a diketopiperazine and an active agent which may be incorporated into the particle formulation.

Stabilizing agents may be included for conformational stability during the drying process. In addition, these stabilizing agents may further improve the aerodynamics or bioavailability of the dry powder diketopiperazine-insulin particle formulations of the present invention. Such stabilizing agents may comprise, but are not limited to, sugars, surface modifying agents, surfactants, hydrophobic amino acids such as tryptophan, tyrosine, leucine, phenylalanine, pharmaceutical carriers or excipients, and the like.

Stabilizing agents contemplated by the present invention are those preferably suitable for respiratory and pulmonary administration. In certain embodiments, it is preferred that the stabilizing agent be incorporated simultaneously into the diketopiperazine-insulin particle to produce a homogeneous powder. Alternatively, the stabilizing agent may be separately prepared in a dry powder form and combined with the spray dried diketopiperazine-insulin particle by blending.

In other instances, powder carriers may be employed such as, but not limited to carbohydrates, e.g., monosaccharides such as fructose, galactose, glucose, D-mannose, sorbose, and the like; disaccharides, such as lactose, trehalose, cellobiose, and the like; cyclodextrins, 2-hydroxypropyl-β-cyclodextrin; and polysaccharides, such as raffinose, maltodextrins, dextrans, and the like; amino acids, such as glycine, arginine, aspartic acid, glutamic acid, cysteine, lysine, and the like; organic salts prepared from organic acids and bases, such as sodium citrate, sodium ascorbate, magnesium gluconate, sodium gluconate, tromethamine hydrochloride, and the like; peptides and proteins, such as aspartame, human serum albumin, gelatin, and the like; alditols, such as xylitol, and the like. A preferred group of carriers may include trehalose, raffinose, maltodextrins, glycine, sodium citrate, tromethamine hydrochloride, human serum albumin, and mannitol. Such powder carriers will usually be crystalline (to avoid water absorption), but might in some cases be amorphous or mixtures of crystalline and amorphous forms. The size of the stabilizing agent particles may be selected to improve the flowability of the spray dried powder product.

Sugars as contemplated by the present invention include, but are not limited to, dextrose, lactose, and mannitol.

Surfactants as contemplated by the present invention include, but are not limited to, polysorbate 80 (PS80), lecithin, phosphatidylcholine, DPPC, sodium dodecylsulfate, and ionic detergents.

5. Method for Coating Microparticles

The procedure for coating crystalline microparticles, such as preformed crystalline microparticles, with active agents is described generally as follows: crystalline microparticles previously formed by precipitation, or another method, are suspended in liquid medium, such as water; and the medium is adjusted to alter the particles' surface either before or after addition of active agent. At this point the active agent will adsorb to the microparticle surface and after an interval of time (for example <1, 1, 2, 3, 4, 5, 6, 7, 8, 9, or 10 minutes; preferably from <1 to at least 5 minutes) the loading process will be complete. The liquid medium may then be removed by spray-drying.

6. Promoting Adsorption of Active Agents

Adsorbing active agent to the surface of a crystalline microparticle can involve altering the properties of the active agent in a solution or fluid suspension under various solution conditions, thereby promoting adsorption to the microparticle surface and reducing the amount of active agent remaining in solution. Alteration or modifications to the active agent may occur with the use of modifiers such as, but not limited to, chaotropes and kosmotropes, salts, organics such as, but not limited to, alcohols, osmolytes, and surfactants. These modifiers can act on the active agent to alter its chemical potential and thereby its structure, flexibility, rigidity or stability, without chemically altering the agent itself. The term "chemical potential" is well known to one of ordinary skill. In embodiments of the present invention, "chemical potential" refers to the free energy necessary to drive a chemical reaction such as, for example, interaction between an active agent and a solvent or the adsorption of active agent onto a microparticle. The term "energetically favorable" as used herein refers to the lowering of the free energy levels of the adsorbed states of the active agent onto the microparticle in relation to the free energy level of uncoated microparticle, or unbound active agent and/or the insoluble forms (including aggregation or precipitation) of the active agent. The term "structure" as used herein refers to the secondary structure of the active agent molecule and includes the alpha-helical formation, beta sheets, or random coil (unordered) of the active agent molecule, such as a protein. Additionally, the term structure may also include teritary and quaternary structures of the molecule but is not limited to such and may also refer to the self association, aggregation, multimerization, dimerization, and the like, of a molecule. The term "stability" as used herein refers to the stabilization or destabilization of the structure of the active agent in the presence of the modifier.

In addition, altering the properties of the active agent in a solution or fluid suspension are likely to affect the interactions due to hydrophobic properties, hydrogen bonding properties, and electrostatic properties of the active agent and/or microparticle.

Hydrophobic interactions are associations of non-polar groups with each other in aqueous solutions because of their insolubility in water. Hydrophobic interactions can affect a number of molecular processes including, but not limited to, structure stabilization (of single molecules, complexes of two or three molecules, or larger assemblies) and dynamics, and make important contributions to protein-protein and protein-ligand binding processes. These interactions are also known to play a role in early events of protein folding, and are involved in complex assembly and self-assembly phenomena (e.g., formation of membranes).

Hydrogen bonding interactions are especially strong dipole-dipole forces between molecules; a hydrogen atom in a polar bond (e.g., H—F, H—O or H—N) can experience an attractive force with a neighboring electronegative molecule or ion, which has an unshared pair of electrons (typically an F, O, or N atom on another molecule). Hydrogen bonds are responsible for the unique properties of water and are very important in the organization of biological molecules, especially in influencing the structure of proteins and DNA.

Electrostatic interactions are attractions between opposite charges or repulsions between like charges that grow stronger as the charges come closer to each other. Electrostatic interactions constitute a key component in understanding interactions between charged bodies in ionic solutions. For example, the stability of colloidal particles dispersed in a solvent can be explained by considering the competition between repulsive electrostatic interactions and the attractive van der Waals interactions. Electrostatic interactions are also of importance when considering interaction and adhesion between particles.

7. Manipulating Microparticle Surface Properties

As disclosed elsewhere herein, the surface properties of the microparticle can be manipulated by various means. The microparticle surface properties that can be manipulated include, but are not limited to, electrostatic, hydrophobic, and hydrogen bonding properties. In various embodiments these manipulations are carried out in the absence or presence of the active agent, or before or after the microparticles and the active agent are mixed together. When the manipulation takes place in the presence of the active agent, for example by altering solution condition, there can also be effects on the active agent that will modify its affinity for the surface. Thus in some embodiments of the present invention, coating of the microparticle can involve manipulation of surface properties and modification of properties of the active agent. Methods directed to the latter are disclosed in U.S. Pat. No. 7,803,404 entitled METHOD OF DRUG FORMULATION BASED ON INCREASING THE AFFINITY OF ACTIVE AGENTS FOR CRYSTALLINE MICROPARTICLE SURFACES and which is incorporated herein by reference in its entirety.

Electrostatic interactions are attractions between opposite charges or repulsions between like charges that grow stronger as the charges come closer to each other. Electrostatic interactions constitute a key component in understanding interactions between charged bodies in ionic solutions. For example, the stability of colloidal particles dispersed in a solvent can be explained by considering the competition between repulsive electrostatic interactions and the attractive van der Waals interactions. Also, the chemical functionality (for example, but not limited to COON, NH, etc.) of the microparticle surface can be utilized as the counter ion to an ionized active agent such that the active agent/particle composite comprises a salt. Electrostatic interactions are also of importance when considering interaction and adhesion between particles.

Altering the pH of the surrounding solution system can change electrostatic properties of ionizable crystalline microparticles in suspension. Changing the pH of the solution changes the ionization of a microparticle such that active agent adsorbs to the microparticle surface. Microparticles composed of FDKP (3,6-bis[N-fumaryl-N-(n-butyl)amino] 2,5-diketopiperazine) are ionizable. The microparticles are insoluble in water below pH 3.5 but solubility increases rapidly between pH 3.5 and 5.0, presumably due to the ionization of the carboxyl groups. The FDKP microparticle is partially ionized at pH 5 prior to complete dissolution at higher pH, which can be observed indirectly via ultrasonic spectroscopy. In one embodiment, diketopiperazine microparticles are suspended in an acidic solution, active agent is added to the suspension, and the pH of the solution is raised after the active agent and microparticles are mixed together. The increased pH alters the surface properties of the microparticles to create an environment in which the active agent has a higher affinity for the microparticle than for the solvent.

Alternatively, the pH of the microparticle suspension can be raised immediately prior to addition of active agent to the solution. The surface charge properties of the microparticle are altered by the change in pH such that active agent has a higher affinity for the microparticle than for remaining in solution and is adsorbed to the microparticle surface upon addition.

8. Other Methods of Manipulating the Surfaces of Microparticles

In addition to electrostatic properties, other properties of a microparticle surface can be exploited to control adsorption of active agent. Microparticles containing compounds with imidazole, pyridine, Schiff bases, ketone, carboxylic acid bioisosteres, amides, or other functional groups that can exist in multiple structures could be manipulated to modify surface properties.

Hydrophobic interactions are associations of non-polar groups with each other in aqueous solutions because of their insolubility in water. Hydrophobic interactions can affect a number of molecular processes including, but not limited to, structure stabilization (be it of single molecules, complexes of two or three molecules, or larger assemblies) and dynamics, and make important contributions to protein-protein and protein-ligand binding processes. These interactions are also known to play a role in early events of protein folding, and are involved in complex assembly and self-assembly phenomena (e.g., formation of membranes).

Hydrophobic interactions can be manipulated by changing the protonation of crystalline microparticles composed of histidine. Protonating the histidine will reduce the nucelophilicity of the crystalline microparticles and impart a positive charge.

Hydrogen bonding interactions are especially strong dipole-dipole forces between molecules; a hydrogen atom in a polar bond (e.g., H—F, H—O or H—N) can experience an attractive force with a neighboring electronegative molecule or ion, which has an unshared pair of electrons (usually an F, O or N atom on another molecule). Hydrogen bonds are responsible for the unique properties of water and are very important in the organization of biological molecules, especially in influencing the structure of proteins and DNA.

In the present invention, the hydrogen bonding properties of the microparticle surface can be controlled by chemical derivatization. Hydrogen bond donors/acceptors can be added chemically to alter the microparticle surface. For example, the hydrogen in an N—H bond can undergo hydrogen bonding to the oxygen in a C=O bond. If the N—H is replaced by an N—CH$_3$, then this particular hydrogen bonding interaction is removed. Likewise, replacement of the C=O group with a C=C group also removes this particular bonding interaction.

Microparticles with surfaces containing ionizable aromatic groups are polar when ionized but hydrophobic in their un-ionized state. Starting with protonated surfaces and manipulating solution conditions to reduce particle surface ionization causes hydrophobic or aromatic active agents to coat the microparticle surface.

Microparticles with ketone surface groups could be manipulated by changing the solution polarity. By reducing solvent polarity (adding low polarity organic solvents to an aqueous solution) the enol-form is made the predominant species at the particle surface. This enol-form is a hydrogen bond donor whereas the keto-form is a hydrogen bond acceptor. The adsorption of nitrogen-containing drugs onto the microparticle surface is promoted in this manner.

Microparticles with surface groups that undergo pH- or temperature-induced isomerization can also be induced to adsorb drug molecules by manipulating solution conditions. In the case of these surfaces, the introduction of a kink in a linear surface group due to isomerization increases the mobility (fluidity) of the groups at the microparticle surface. This allows the surface to form more contacts with the active agent than are possible with an ordered surface. If the additional interactions with the active agent are each favorable, then the net interaction energy becomes favorable and the drug adsorbs to the microparticle surface.

EXAMPLES

The following examples are included to demonstrate preferred embodiments of the present invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effect of Atomization Pressure on Aerodynamics, Stability, and Aggregation

Diketopiperazine derivative, 3,6-bis[N-fumaryl-N-(n-butyl)amino]-2,5-diketopiperazine (also referred to as 3,6-di(fumaryl-4 aminobutyl)-2,5-diketopiperazine, fumaryl diketopiperazine or FDKP; also termed (E)-3,6-bis[4-(N-carboxy-2-propenyl)amidobutyl]-2,5-diketopiperazine) were precipitated and washed. Insulin was loaded onto the FDKP particles by adjustment to a pH of approximately 4.45, and the FDKP-insulin particles were spray dried to obtain a FDKP-insulin dry powder. A pH of about 4.45 was found to increase the binding of insulin to FDKP particles as disclosed in U.S. patent application Ser. Nos. 11/532,063 and 11/532,025 both filed on Sep. 14, 2006, and U.S. Provisional Patent Application Ser. No. 60/717,524, filed on Sep. 14, 2005.

The dry powders were characterized for various aerodynamic properties (% RF, cartridge emptying, % RF/fill, mass median aerodynamic diameter [MMAD], and geometric standard deviation [GSD]).

Table 1 and FIG. 1 demonstrate the effect of the atomization (nozzle) pressure on the aerodynamic performance of the particles. The nozzle pressures ranged from 0.4 bar to 1.1 bar (Table 1). The respirable fraction on fill % RF on Fill) improved as the atomization pressure was increased from 0.4 bar to 1.1 bar.

TABLE 1

Effect of atomization pressure on aerodynamic properties. Outlet temperature was 75° C.

| Atomization Pressure (bar) | Inlet T (° C.) | % RF delivered | % Cartridge Emptying | % RF fill | MMAD (µm) | GSD |
|---|---|---|---|---|---|---|
| 0.4 | 105 | 34.7 | 95.5 | 33.1 | 2.7 | 2.2 |
| 0.5 | 105 | 30.3 | 92.1 | 27.9 | 3.3 | 2.3 |
| 0.6 | 105 | 39.4 | 95.6 | 37.7 | 2.5 | 2.3 |
|  | 120 | 45.5 | 91.9 | 41.8 | 2.7 | 2.2 |
|  | 120 | 45.4 | 92.2 | 41.9 | 2.5 | 2.2 |
|  | 140 | 42.4 | 91.4 | 38.8 | 2.5 | 2.2 |
| 0.7 | 105 | 48.2 | 92.7 | 44.7 | 2.7 | 2.2 |
|  | 110 | 71.9 | 68.9 | 49.5 | 2.3 | 2.0 |
|  | 120 | 57.7 | 77.6 | 44.8 | 2.5 | 2.0 |
|  | 130 | 63.5 | 71.6 | 45.5 | 1.9 | 2.0 |
| 0.9 | 110 | 68.4 | 70.2 | 48.0 | 2.3 | 2.0 |
|  | 120 | 68.3 | 74.9 | 51.2 | 2.1 | 2.0 |
|  | 130 | 55.4 | 90.2 | 49.9 | 2.7 | 2.0 |
| 1.1 | 110 | 64.2 | 84.0 | 54.0 | 2.5 | 1.9 |
|  | 120 | 70.4 | 70.8 | 49.8 | 2.0 | 2.0 |
|  | 130 | 71.7 | 74.9 | 53.7 | 2.2 | 2.0 |

Figure 2A:
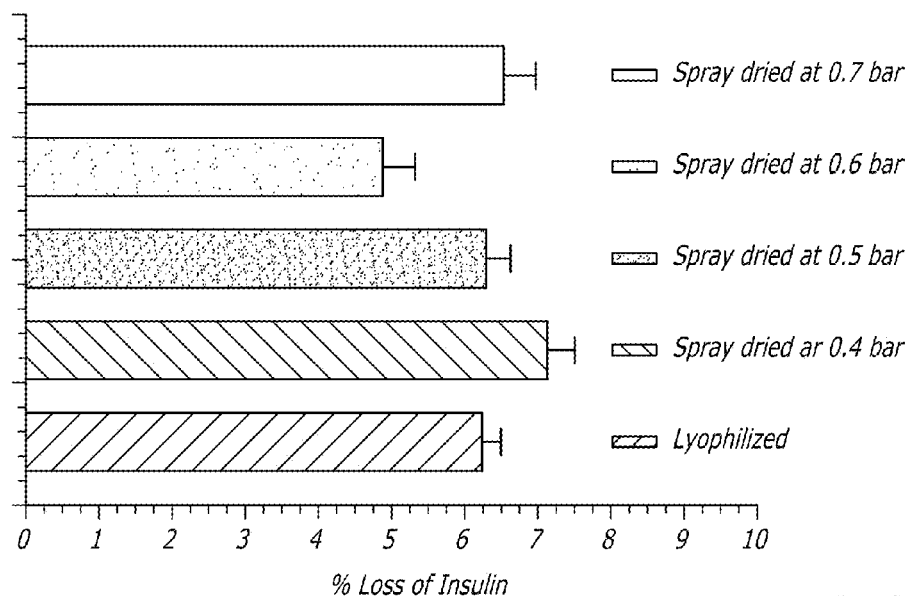
FIGS. 2A-2E. Evaluation of the accelerated stability of diketopiperazine-insulin formulations. The accelerated stability conditions were 40° C. and 75% RH (relative humidity) for 10 days. A reduction in insulin loss in the spray-dried formulations is depicted in FIG. 2A.
Figure 2B:
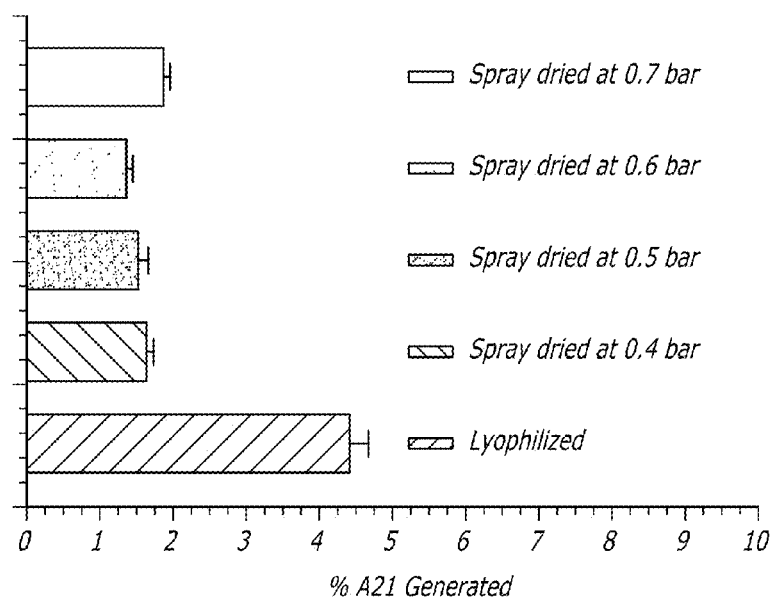

The stability of the insulin was assessed as the percent loss of insulin (FIG. 2A) and the percent conversion to insulin degradation product A21-desamido insulin (% A21) under stress conditions (10 days at 40° C., 75% RH) (see FIG. 2B). For comparison, the bottom bar in each figure represents data obtained with freeze dried particles. The data demonstrate that, as the atomization pressure was increased, there was a general trend toward increased stability of the insulin in the diketopiperazine-insulin particles. Less formation of the A21 insulin degradation product was observed in all of the spray-dried particles as compared to freeze-dried particles (FIG. 2B).

Figure 2C:
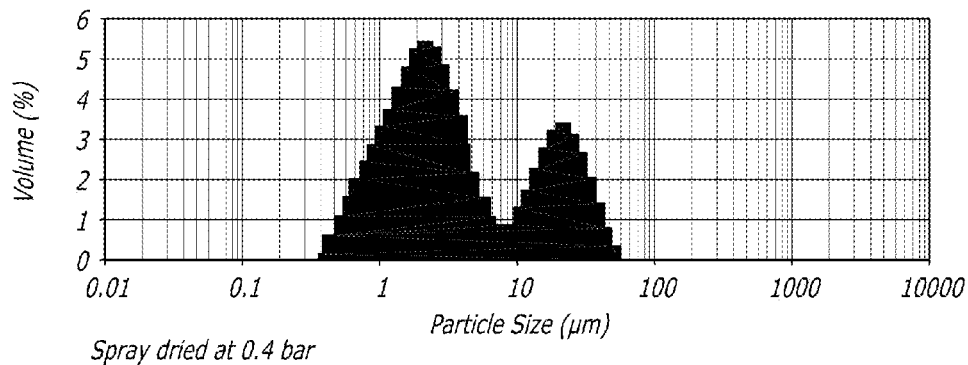
Figure 2D:
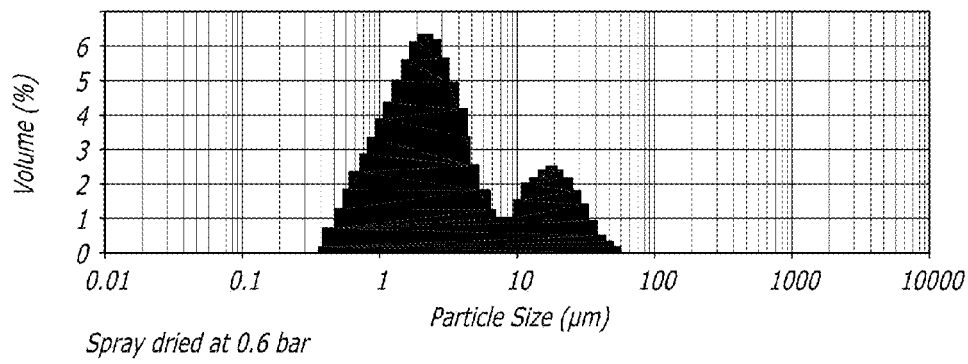
Figure 2E:
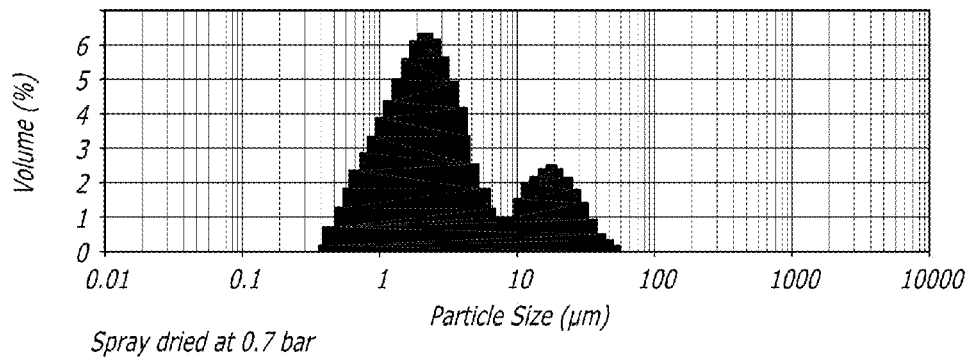

To assess aggregation of the primary particles, the particle size distribution was determined from laser diffraction of a suspension of spray-dried particles using a Malvern Mastersizer 2000. Under the above trial conditions, a trend towards decreased aggregation of the primary diketopiperazine-insulin particles was observed with increased atomization pressure (FIGS. 2C-2E). It is observed that the size of the peak to the right, representing aggregated particles, decreases as the atomization pressure increases from 0.4 bar (FIG. 2C) to 0.6 bar (FIG. 2D), to 0.7 bar (FIG. 2E).

Example 2

Effect of Inlet Temperatures on Aerodynamics, Stability, and Particle Aggregation Using particles prepared as above, spray dryer inlet temperature and process scalability were evaluated as shown in Table 2 below. In these experiments, the inlet temperature was varied from 105° C. to 140° C. and the outlet temperature was held constant at 75° C. The nozzle pressure was held constant at 0.6 bar.

It was observed that the increased inlet temperatures required an increase in the spray rate to maintain a consistent outlet temperature (Table 2). The increased spray rates produced dried particles at a greater production rate. The aerodynamics of the spray dried particles were assessed (Table 2). The % RF on Fill remained consistent over the temperature range studied (FIG. 3).

TABLE 2

Effect of inlet temperature on particle aerodynamics. Nozzle pressure was maintained at 0.6 bar and the outlet temperature was 75° C.

| Scale (g) | Spray Rate (g/min) | Inlet Temp. (° C.) | % RF | % cartridge emptying | % RF on Fill | MMAD (μm) | GSD |
|---|---|---|---|---|---|---|---|
| 11.3 | 4.4 | 105 | 39.4 | 95.6 | 37.7 | 2.5 | 2.3 |
| 11.3 | 7.6 | 120 | 45.5 | 91.9 | 41.8 | 2.7 | 2.2 |
| 45.2 | 7.6 | 120 | 42.4 | 91.4 | 38.8 | 2.5 | 2.2 |
| 11.3 | 12.2 | 140 | 45.4 | 92.2 | 41.9 | 2.5 | 2.2 |

Figure 4A:
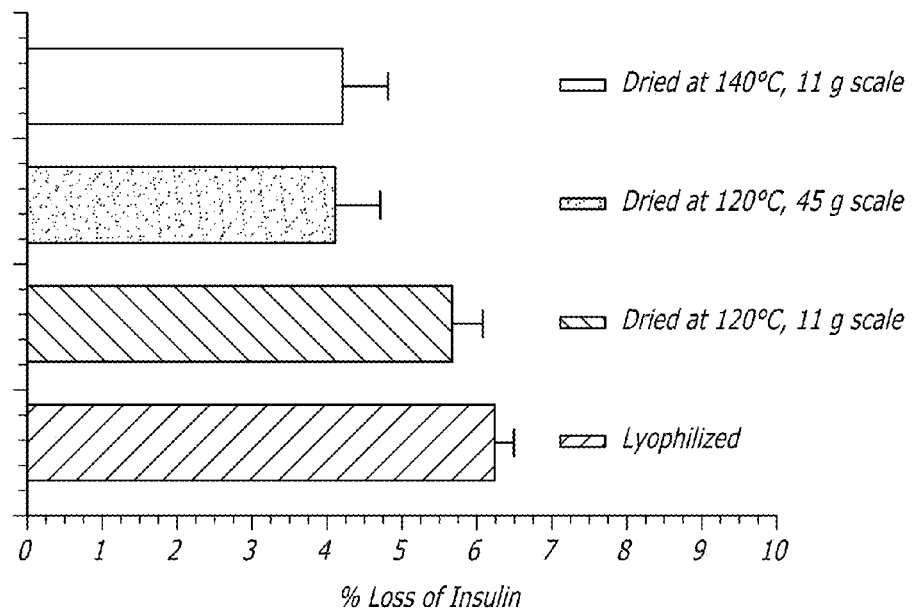
FIGS. 4A-4F. Demonstration that increased inlet temperature (drying rate) did not negatively impact the stability of the formulations. The accelerated stability conditions were 40° C. and 75% RH for 10 days.
Figure 4B:
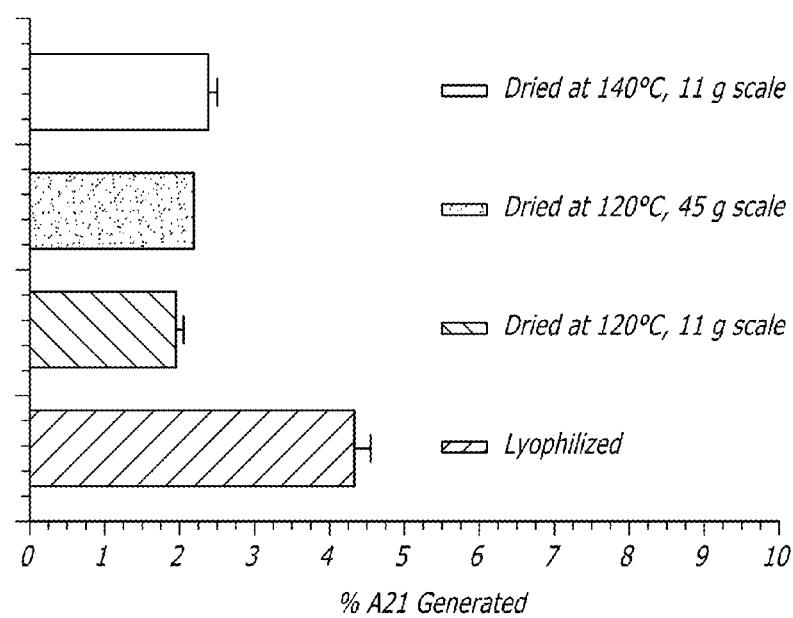
Figure 4C:
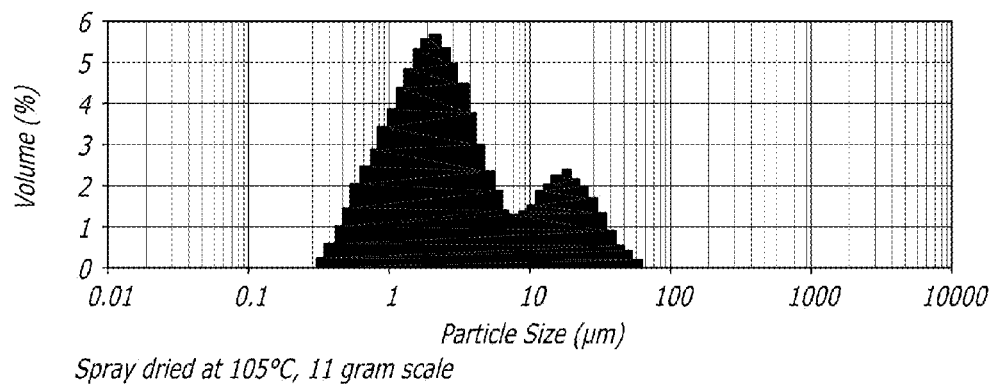
Figure 4D:
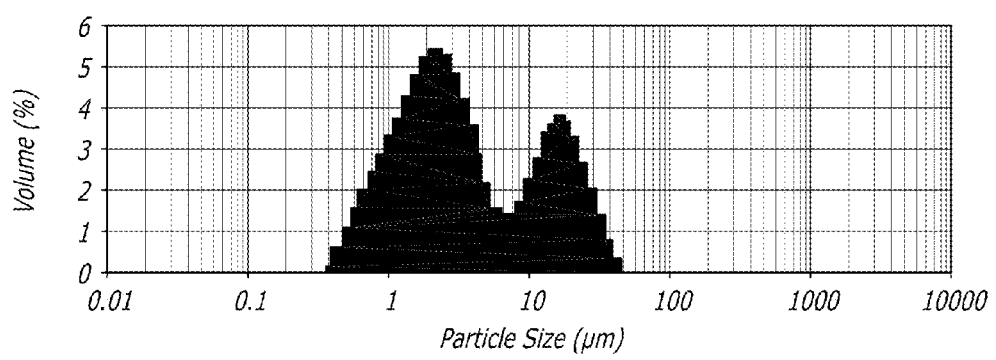
Figure 4E:
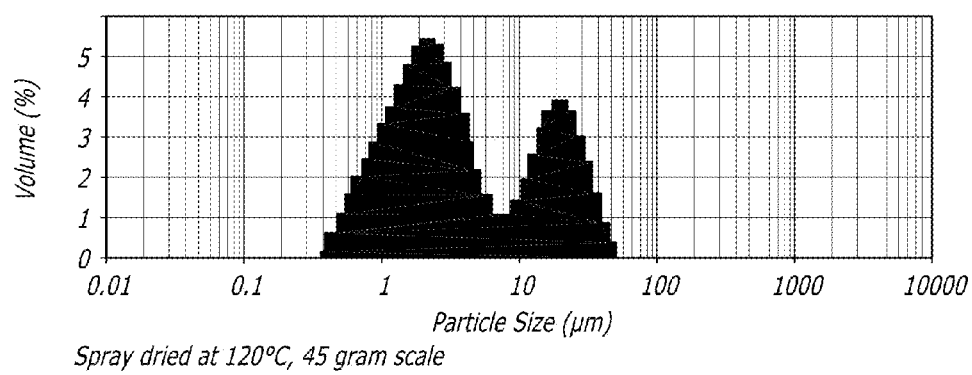
Figure 4F:
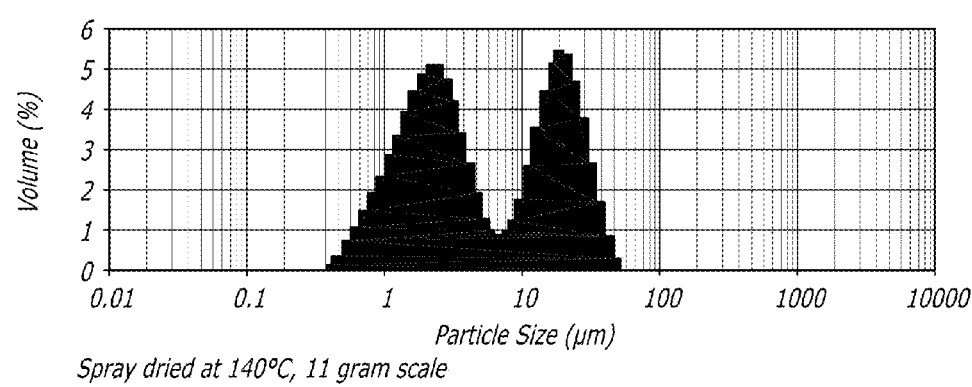

Further, the data demonstrated that increasing the inlet temperature (drying rate) did not negatively impact the stability of the insulin on the particles. There was a trend toward increased insulin stability with increasing inlet temperature. Stability was measured as insulin lost and A21 formed (FIGS. 4A and 4B) after 10 days at 40° C./75% RH. However, under the above trial conditions, a trend toward increase aggregation of the primary diketopiperazine-insulin particles was observed with an increase in the inlet temperature (FIGS. 4C-4F).

Example 3

Insulin Recovery and Distribution

In these experiments, a known mass of diketopiperazine particles was suspended in water. Enough insulin solution of known concentration was added to the suspension to give a theoretical composition of 11.4% insulin. The fumaryl diketopiperazine-insulin slurry was titrated to a pH of approximately 4.45 prior to spray drying.

Insulin distribution across particles was assessed as shown in FIG. 5A. These experiments were conducted using an Andersen Cascade Impactor. The powder was filled into cartridges and discharged through a MedTone® inhaler into the Andersen cascade impactor. (The MedTone® inhaler is described in U.S. patent application Ser. No. 10/655,153 entitled "Unit Dose Cartridge and Dry Powder Inhaler" which is incorporated herein by reference for all it contains regarding the inhaler device). The impactor classifies the particles by aerodynamic size. After discharge, the powder was recovered from each stage and assayed for insulin content (load). Insulin is shown to be evenly distributed throughout the formulation. Increasing the scale (grams of the powder), as shown in Table 2 above, by a factor of 4 was also found to be acceptable.

Particle morphology of the spray-dried and lyophilized particles was compared by scanning electron microscopy (SEM). FIG. 5B-5E shows the particle morphologies for the lyophilized formulation (FIGS. 5B and 5D) are comparable to those for the spray-dried formulation (FIGS. 5C and 5E).

Summary of Examples 1-3

The above data, show that: 1) increasing the atomization pressure decreased the aggregation of the primary particles; 2) increasing the inlet temperature had little impact on the particles aerodynamics; 3) increasing the inlet temperature was not observed to have a negative impact on the stability of the insulin; 4) increasing the inlet temperature resulted in greater aggregation of the primary particles; 5) spray-dried particles had increased insulin stability when compared to lyophilized particles of identical composition; and 6) spray-dried particles had similar morphology as lyophilized particles.

Example 4

Determination of Spray-drying Parameters to Maximize Aerodynamic Performance

Inlet temperature and atomization pressure were further evaluated using inlet temperatures of 110, 120 and 130° C. and atomization pressures of 0.7, 0.9, and 1.1 bar (Table 3).

TABLE 3

Effect of spray-drying parameters on particle aerodynamics

| Atomization pressure (bar) | Inlet Temperature (° C.) | % RF | % Cartridge emptying | % RF on fill | MMAD (μm) | GSD |
|---|---|---|---|---|---|---|
| 0.7 | 110 | 71.9 | 68.9 | 49.5 | 2.3 | 2.0 |
| 0.7 | 120 | 57.7 | 77.6 | 44.8 | 2.5 | 2.0 |
| 0.7 | 130 | 63.5 | 71.6 | 45.5 | 1.9 | 2.0 |
| 0.9 | 110 | 68.4 | 70.2 | 48.0 | 2.3 | 2.0 |
| 0.9 | 120 | 68.3 | 74.9 | 51.2 | 2.1 | 2.0 |
| 0.9 | 130 | 55.4 | 90.2 | 49.9 | 2.7 | 2.0 |
| 1.1 | 110 | 64.2 | 84.0 | 54.0 | 2.5 | 1.9 |
| 1.1 | 120 | 70.4 | 70.8 | 49.8 | 2.0 | 2.0 |
| 1.1 | 130 | 71.7 | 74.9 | 53.7 | 2.2 | 2.0 |

FIG. 6A summarizes the results of Table 3 as the % RF on fill versus the atomization pressure; FIG. 6B summarizes the results as % RF on fill versus the inlet temperature. Thus, the data show that increasing atomization pressure leads to improved aerodynamic performance and inlet temperature does not affect this parameter.

Example 5

Figure 7A:
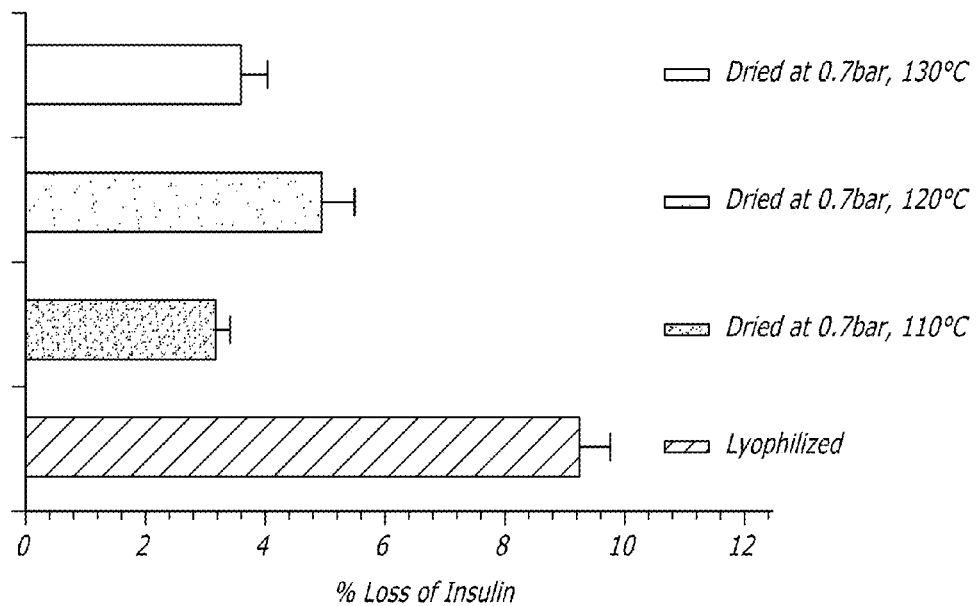
FIGS. 7A-7K. Demonstration that insulin stability increases at higher inlet temperatures and atomization pressures.
Figure 7B:
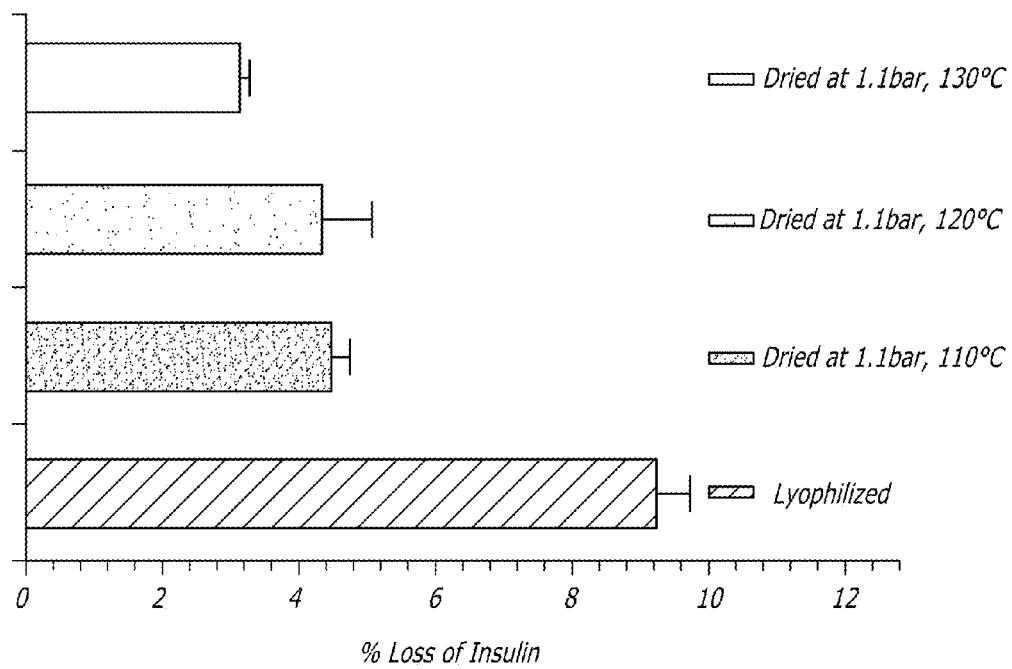
Figure 7C:
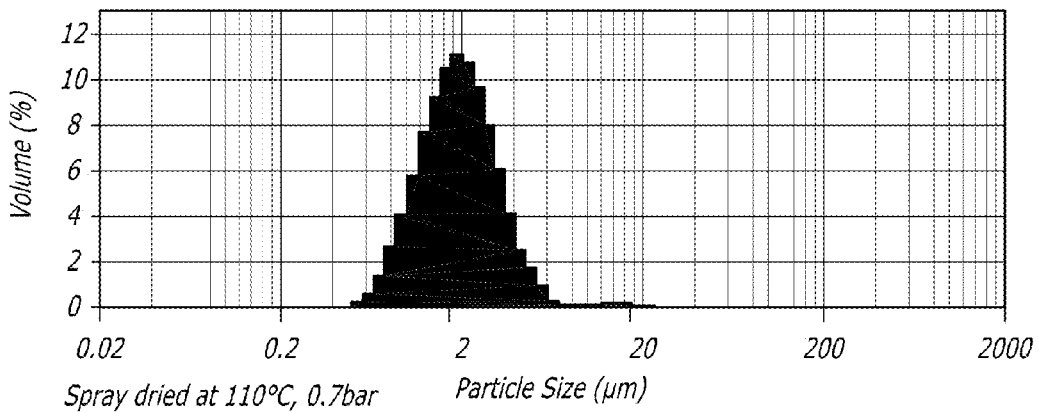
Figure 7D:
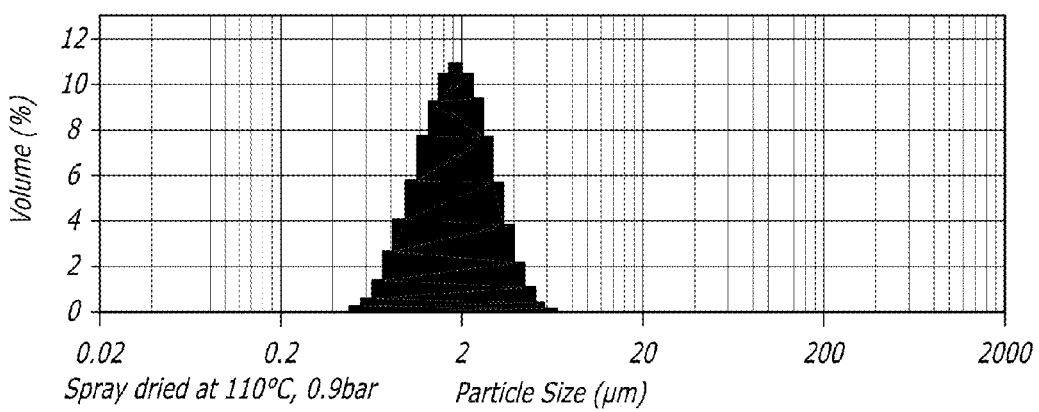
Figure 7E:
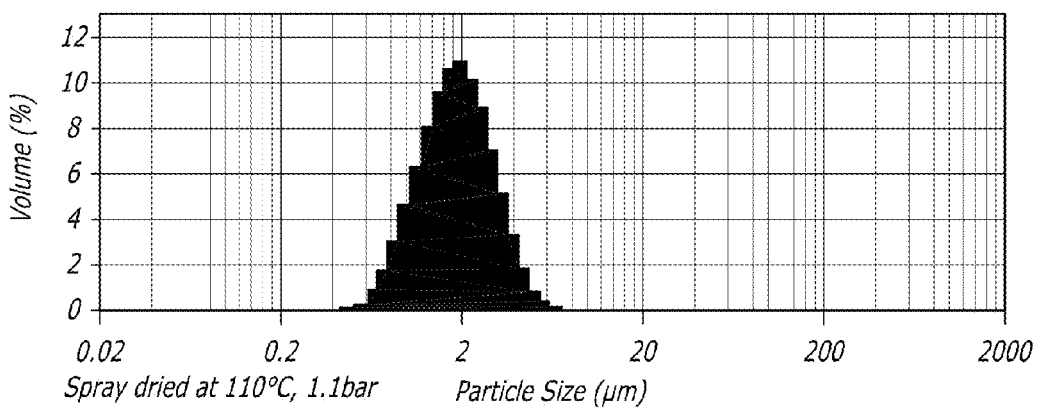
Figure 7F:
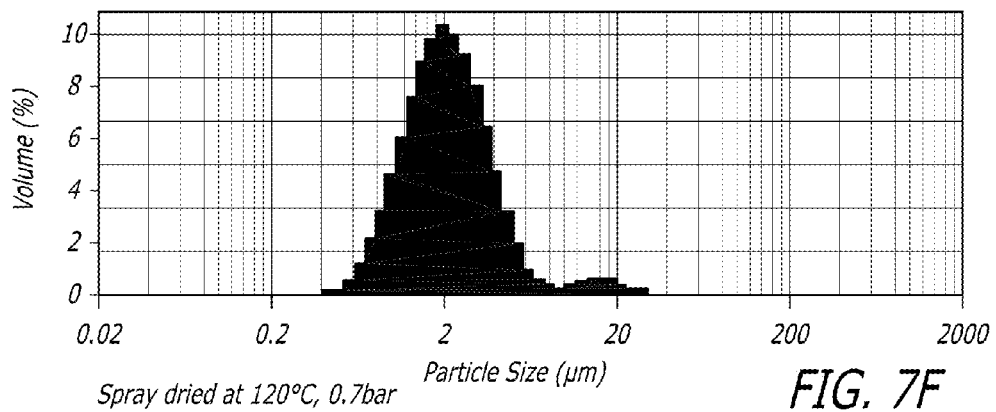
Figure 7G:
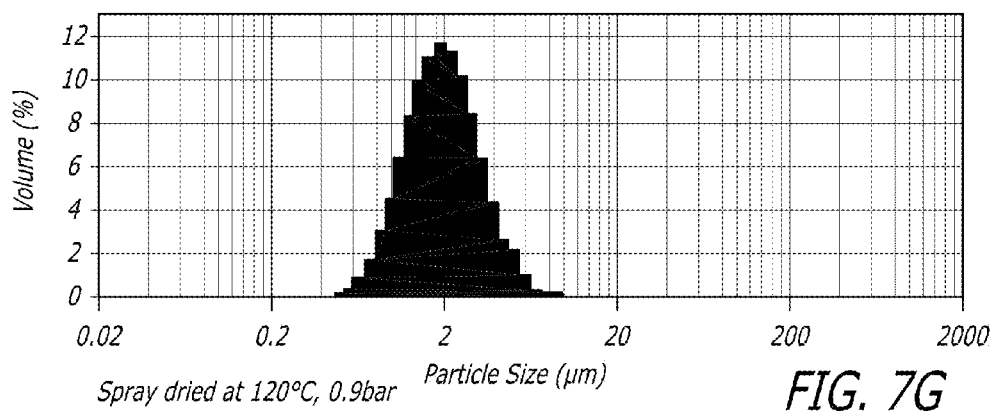
Figure 7H:
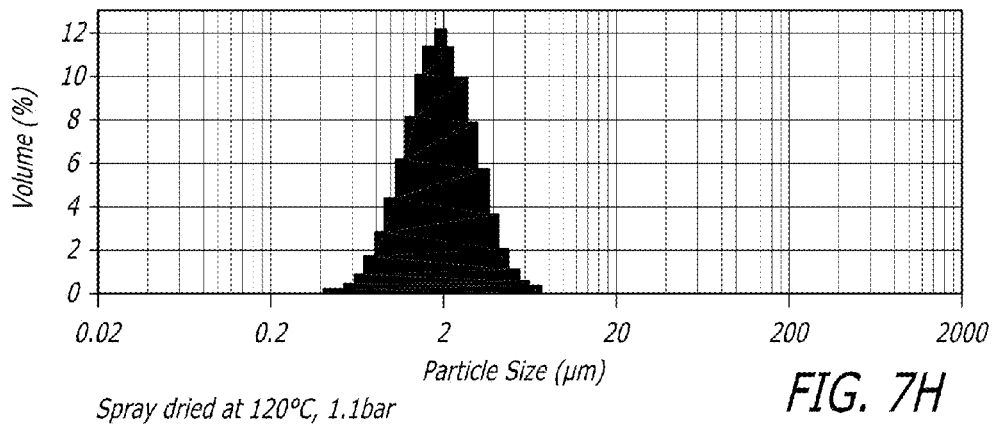
Figure 7I:
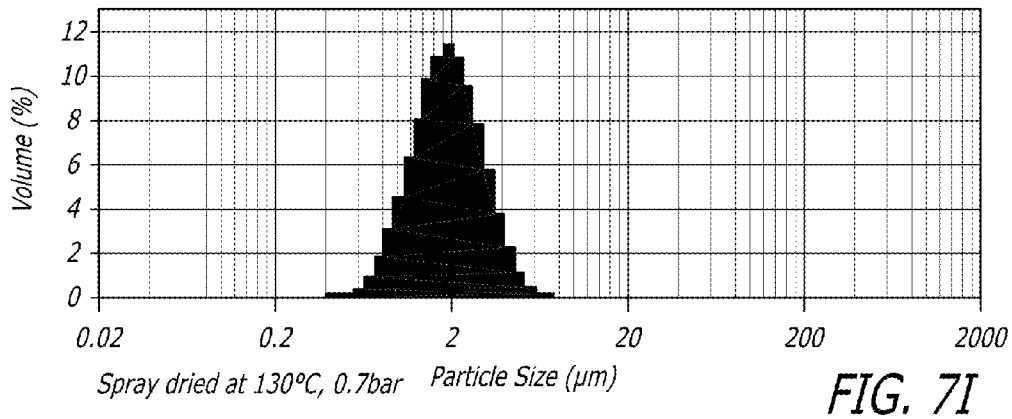
Figure 7J:
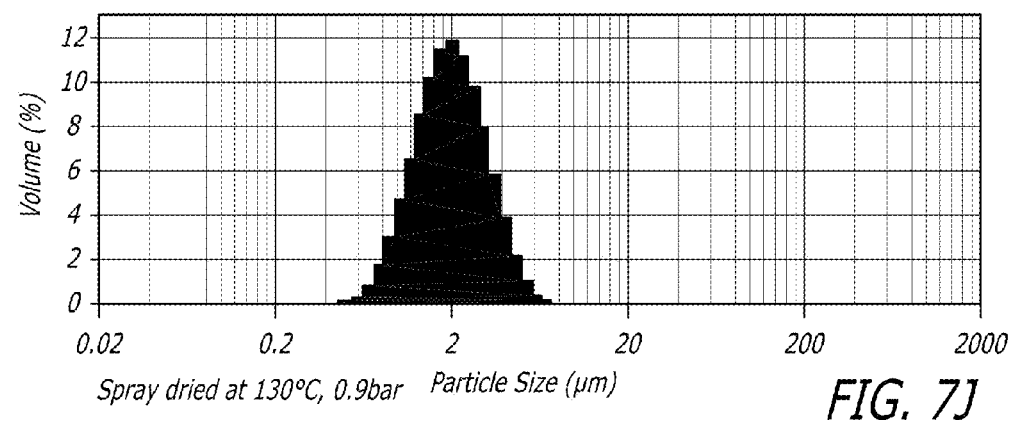
Figure 7K:
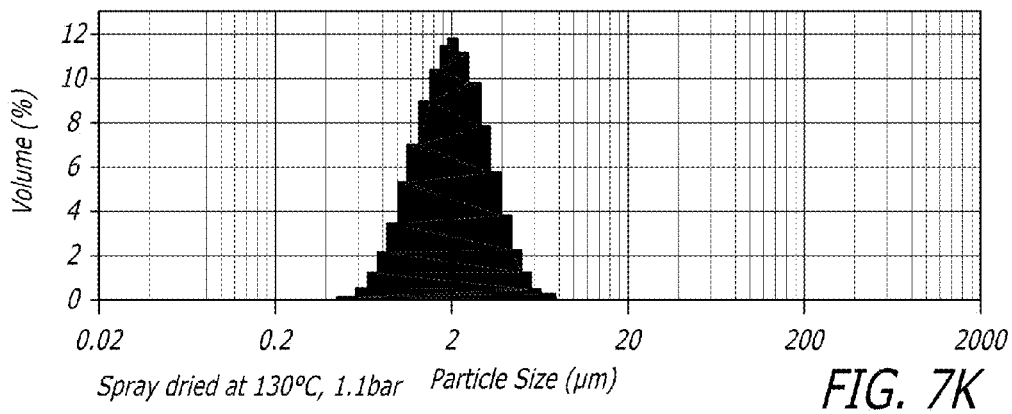

Effect of Inlet Temperature and Atomization Pressure on Stability and Aggregation The samples listed in Table 3 were analyzed for insulin stability and particle aggregation. As shown in FIGS. 7A and 7B, the results were consistent with those of Examples 1-3 in that the spray-dried samples showed less insulin loss than comparable lyophilized powders (the bottom bar in FIGS. 7A and 7B; loading of the particles used in the lyophilized samples included adjustment to pH 4.5, which as discussed in Example 1 above, increases the binding of insulin to FDKP particles).

The aggregation of the primary diketopiperazine-insulin particle was assessed under the conditions of increased inlet temperature and increased atomization pressure (FIGS. 7C-7K) The particle size distributions by laser diffraction were generally insensitive to atomization pressure and temperature over the ranges covered in this example. A small degree of aggregation was observed at 0.7 bar and inlet temperatures of 110° C. and 120° C., but a unimodal distribution was obtained at all other conditions.

The results for the spray-dried samples as compared to the lyophilized samples show: 1) the atomization pressure can be increased to improve aerodynamics; 2) the inlet temperature has negligible effect on % RF on Fill; 3) insulin stability increases with increased inlet temperature; and 4) the increased inlet temperature and atomization pressure reduced aggregation of the primary insulin particles.

Example 6

Insulin Pharmacodynamics with Spray-dried Particles

Figure 8:
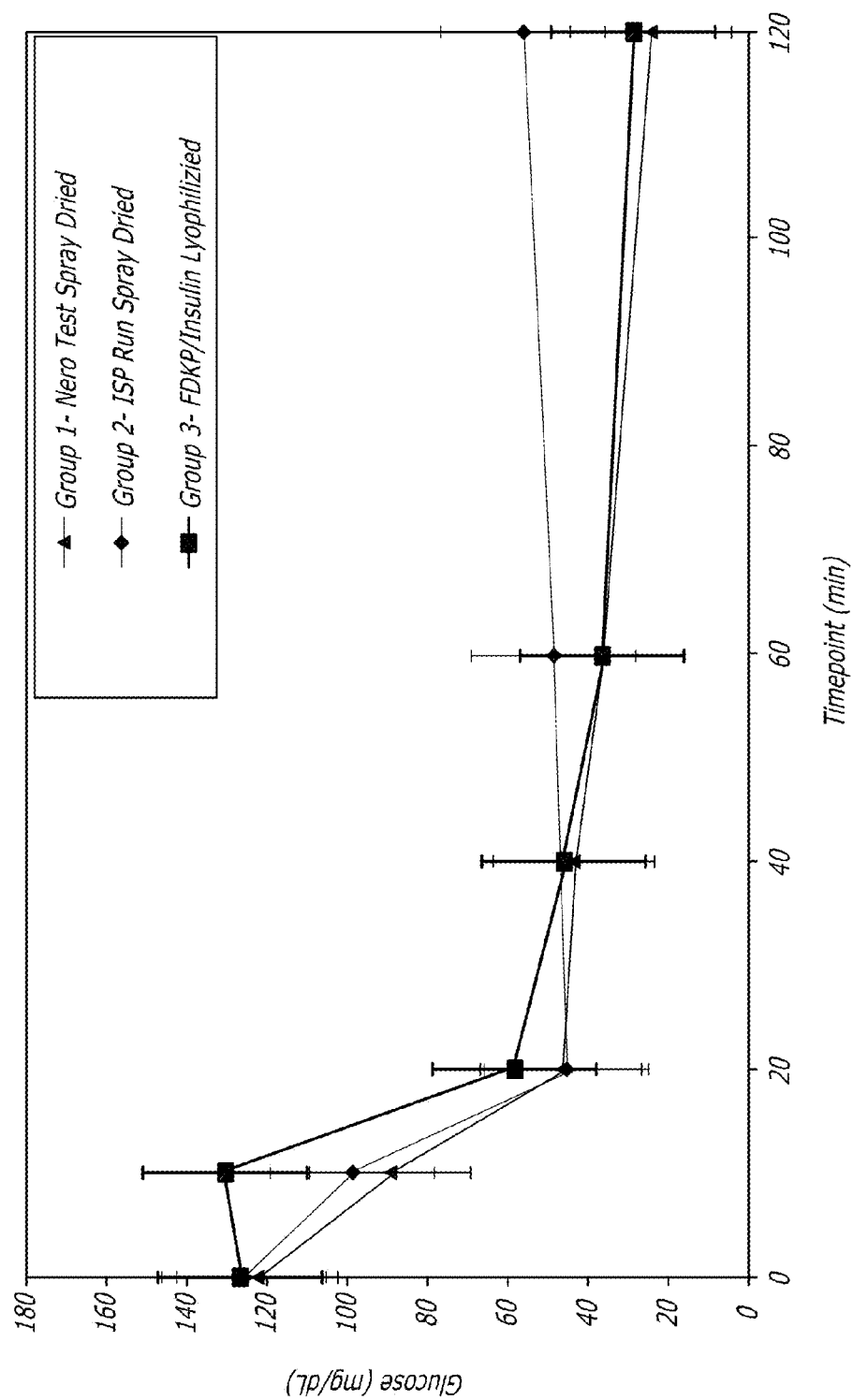
FIG. 8. Comparison of pharmacodynamic profiles (blood glucose reduction) following insufflation of 11.4% lyophilized FDKP/Insulin and 11.4% spray dried FDKP/Insulin in rats. Each animal received 3 mg of powder containing 11.4% insulin by weight. Each group contained 4 animals.

Data from a rat insufflation study indicated that spray-dried FDKP-insulin powder provides at least comparable glucose disposal as provided by lyophilized material. FIG. 8 shows a comparison of pharmacodynamic profiles (blood glucose reduction) following insufflation of lyophilized and spray-dried 11.4% FDKP-insulin particles in rats. The glucose lowering capacity of spray-dried FDKP-insulin powder was found to be equivalent to that of lyophilized FDKP-insulin powder.

Example 7

Aerodynamics and Stability of Spray-dried FDKP-insulin Powder

Fumaryl diketopiperazine (FDKP)-insulin particles were prepared in a manner similar to that described above. That is, particles were mixed with an insulin solution to give particles containing 11.4% insulin by weight, and then the pH adjusted to promote insulin adsorption onto the particles. The resulting particle suspensions were dried by either spray drying or lyophilization. Table 4 shows the comparison of two 200 g lots prepared using a commercial scale spray dryer with similar lyophilized samples. The bulk powders were tested for aerodynamic performance. Additional samples of bulk powders were stored at 40° C./75% RH for 15 days prior to evaluation for insulin loss and formation of A21-desamido insulin. The spray dried powder displayed an average respirable fraction on fill (% RF/fill) of 62%; compared to an average value of 54% for the lyophilized powder. The spray-dried powder also demonstrated superior stability. Insulin loss and A-21 formation of the spray-dried powder were about half that of the lyophilized powder.

TABLE 4

Aerodynamics and stability of spray dried FDKP-insulin powder

| Manufacturing Process | Andersen cascade impactor | | | Accelerated stability | |
| --- | --- | --- | --- | --- | --- |
| | % RF | % Cartridge Emptying | % RF/fill | % Insulin Lost | % A-21 Formed |
| Lyophilized (average of two lots*) | 55 | 98 | 54 | 16.98 | 6.32 |
| Spray dried (average of two lots*) | 66 | 94 | 62 | 8.83 | 2.63 |

*Lots were prepared in a similar manner.

Example 8

Characterization of Spray-dried vs Lyophilized FDKP-insulin Powders

In a further refinement of the process, the feed temperature of the FDKP solution was controlled. Stock solutions of fumaryl diketopiperazine (FDKP) were prepared and cooled to 11° C., 13° C., 15° C., 17° C., or 19° C. and the FDKP particles were precipitated. Two different strategies were employed for loading and drying particles. In one strategy, the precipitated diketopiperazine particles were washed, an insulin solution was added and the pH adjusted to promote adsorption of insulin onto the particle, the mixture was frozen by dropwise addition to liquid nitrogen, and the resulting pellets were lyophilized (freeze-dried) to obtain a diketopiperazine-insulin dry powder. In another parallel protocol the precipitated diketopiperazine particles were washed, an insulin solution was added, the pH adjusted, and the diketopiperazine-insulin particle suspension was spray-dried to obtain a diketopiperazine-insulin dry powder.

Figure 9:
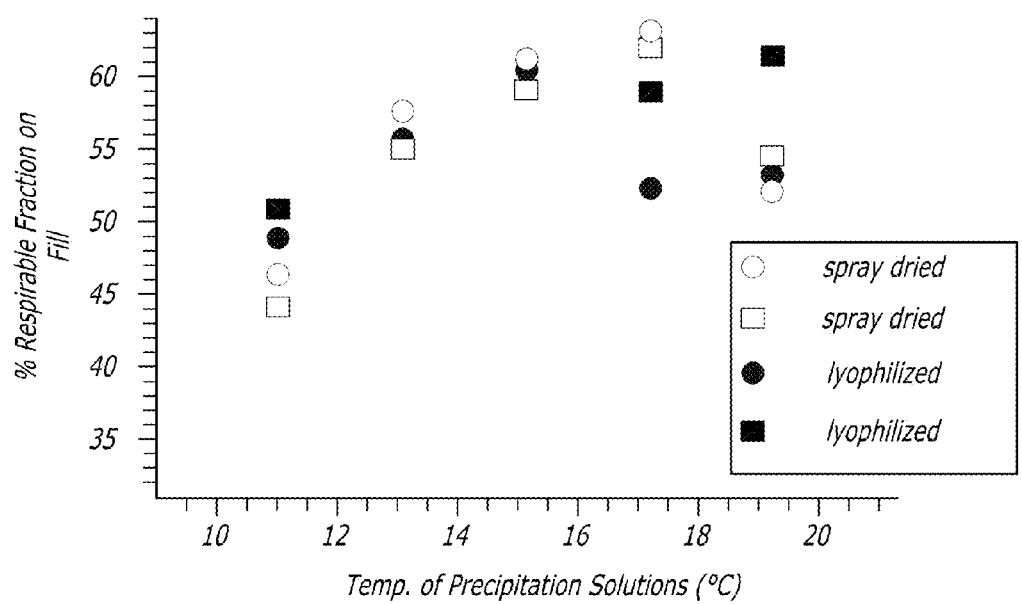
FIG. 9. Aerodynamic performance of FDKP/Insulin powders dried by spray drying or lyophilization. Two sets of suspensions (represented by squares and circles) were tested. Opened symbols represent spray-dried powders; filled symbols represent the lyophilized powders.
Figure 10A:
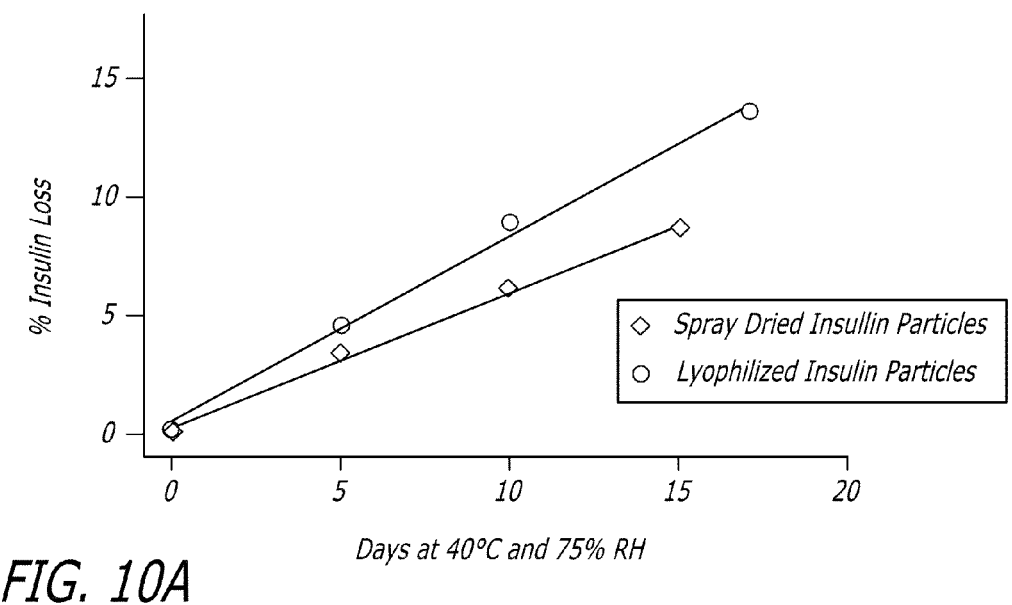
FIGS. 10A-10B. Stability data indicate that insulin loss (FIG. 10A) and A-21 formation (FIG. 10B) are reduced in the spray dried powder compared to the lyophilized powder. Both powders were adjusted to pH 4.5 prior to drying.
Figure 10B:
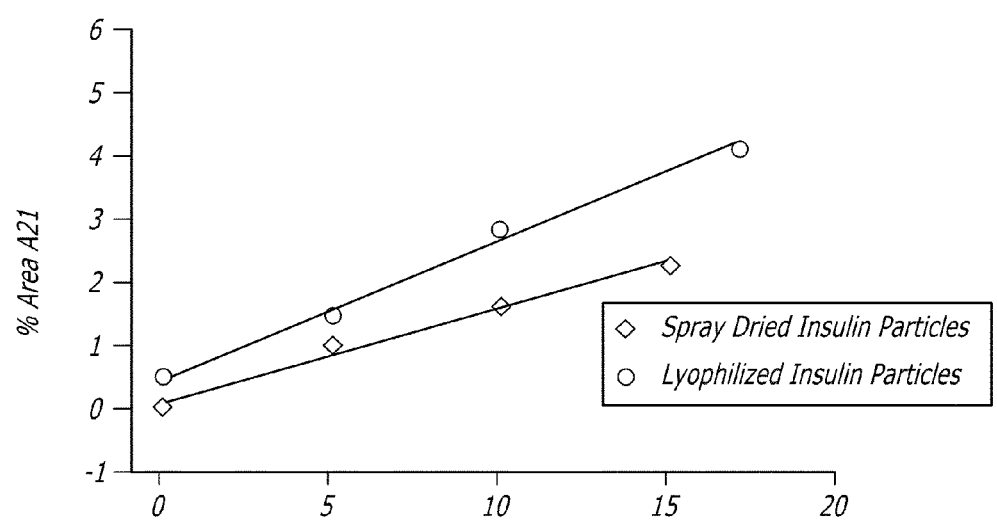

Two sets of replicates were prepared and the dry powders were characterized for aerodynamic performance (% RF/fill, cartridge emptying, mass median aerodynamic diameter [MMAD] and geometric standard deviation [GSD]). These data are summarized in Table 5. The % RF/fill for these samples is shown in FIG. 9. The stability of the powders is compared in FIGS. 10A and 10B. As noted above, the spray-dried powders showed less insulin loss and less formation of A21-desamido insulin than the lyophilized samples.

The bulk density and tapped density of the spray-dried versus the lyophilized FDKP-insulin powder were assessed. The two sets of replicates were characterized for bulk and tapped density. Table 5 shows that the spray-dried powder is more dense (by about a factor of 2) than the lyophilized powder. The bulk and tapped density for the spray-dried materials averaged 0.2 g/cc and 0.29 g/cc respectively. The bulk and tapped densities for lyophilized FDKP-insulin averaged 0.09 g/cc and 0.13 g/cc respectively. These results were unexpected and surprising. This increase in density allows more powder to be placed in a single cartridge, thereby providing for higher dosages.

TABLE 5

Effect of solution temperature on spray-dried and lyophilized FDKP-insulin particles

| Solution temperature (° C.) | Drying method | % RF/fill | % Cartridge Emptying | MMAD (μm) | GSD | Bulk Density (g/cc) | Tapped Density (g/cc) |
|---|---|---|---|---|---|---|---|
| 11 | spray- | 46.0 | 87.0 | 2.8 | 1.9 | 0.171 | 0.260 |
| | dried | 43.8 | 92.1 | 3.2 | 1.8 | 0.182 | 0.267 |
| | lyophi- | 48.4 | 98.4 | 2.7 | 2.1 | 0.077 | 0.121 |
| | lized | 50.2 | 96.1 | 2.4 | 2.1 | 0.080 | 0.122 |
| 13 | spray- | 57.4 | 93.6 | 2.4 | 2.0 | 0.157 | 0.261 |
| | dried | 54.9 | 93.2 | 2.2 | 2.0 | 0.156 | 0.260 |
| | lyophi- | 55.4 | 94.7 | 2.6 | 1.9 | 0.089 | 0.159 |
| | lized | 54.8 | 95.3 | 2.3 | 2.1 | 0.077 | 0.143 |
| 15 | spray- | 60.2 | 93.9 | 2.2 | 2.1 | 0.153 | 0.254 |
| | dried | 58.3 | 94.2 | 2.3 | 2.0 | 0.181 | 0.274 |
| | lyophi- | NM | NM | NM | NM | 0.078 | 0.127 |
| | lized | 59.8 | 94.5 | 2.3 | 2.1 | 0.087 | 0.141 |
| 17 | spray- | 62.4 | 94.0 | 2.4 | 2.0 | 0.177 | 0.269 |
| | dried | 61.5 | 93.4 | 2.2 | 2.0 | 0.186 | 0.291 |
| | lyophi- | 52.3 | 96.1 | 2.4 | 2.1 | 0.087 | 0.141 |
| | lized | 58.6 | 91.8 | 2.2 | 2.1 | 0.083 | 0.134 |
| 19 | spray- | 51.6 | 81.8 | 2.4 | 1.8 | 0.179 | 0.279 |
| | dried | 53.8 | 86.8 | 2.2 | 2.0 | 0.198 | 0.300 |
| | lyophi- | 52.7 | 97.2 | 2.3 | 2.0 | 0.083 | 0.126 |
| | lized | 60.4 | 94.7 | 2.4 | 2.1 | 0.100 | 0.142 |

NM—not measured

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is readily apparent to one skilled in the art that various embodiments and modifications can be made to the invention disclosed herein, without departing from the scope and spirit of the invention.

Following long-standing patent law, and as used herein, the use of the word "a" or "an" when used in conjunction with the term "comprising" in the claims and/or the specification may mean "one," but it is also consistent with the meaning of "one or more," "at least one," and "one or more than one" unless specifically noted.

Recitation of ranges of values herein is merely intended to serve as a shorthand method of referring individually to each separate value falling within the range. Unless otherwise indicated herein, each individual value is incorporated into the specification as if it were individually recited herein.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Other objects, features and advantages of the present invention will become apparent from the detailed description provided herein. It should be understood, however, that the detailed description and the specific examples, while indicating specific embodiments of the invention, are given by way of illustration only, since various changes and modifications within the spirit and scope of the invention will become apparent to those skilled in the art from this detailed description.

What is claimed is:

1. A method of preparing a dry powder medicament with an improved pharmaceutic property, comprising a) providing a solution of a diketopiperazine having acidic or basic side chains;

b) forming particles comprising the diketopiperazine by adjusting the pH of the solution, resulting in a suspension of particles of the diketopiperazine with acidic or basic side chains in a solvent, and optionally loading said particles with an active agent, then c) removing solvent by spray drying to obtain a dry powder, wherein the dry powder has an improved pharmaceutic property as compared to a dry powder obtained by removing solvent by lyophilization, wherein the improved pharmaceutic property is selected from the group consisting of increased density of the powder, increased aerodynamic performance of the powder, and improved stability of the active agent, if present.

2. The method of claim 1, wherein said diketopiperazine is a diketopiperazine having the formula 2,5-diketo-3,6-di(4-X-aminobutyl)piperazine, wherein X is selected from the group consisting of succinyl, glutaryl, maleyl, and fumaryl.

3. The method of claim 2, wherein the diketopiperazine is fumaryl diketopiperazine.

4. The method of claim 1, comprising loading the particle with an active agent prior to the solvent removal step.

5. The method of claim 4, wherein said loading step comprises:

providing a solution or a suspension of the active agent; and adding said solution or suspension of active agent to the suspension of particles of the diketopiperazine with acidic or basic side chains.

6. The method of claim 4, wherein the active agent is selected from the group consisting of insulin, calcitonin, parathyroid hormone 1-34 ((PTH(1-34)), octreotide, leuprolide, RSV peptide, felbamate, cannabinoid antagonists and/or agonists, muscarinic antagonists and/or agonists, heparin, low molecular weight heparin, cromolyn, sildenafil, vardenafil, tadalafil, growth hormone, AZT, DDI, GCSF, lamotrigine, chorionic gonadotropin releasing factor, luteinizing release hormone, β-galactosidase, GLP-1, exendins 1-4 and ghrelin.

7. The method of claim 4, wherein the active agent is a peptide or protein.

8. The method of claim 6, wherein the active agent is insulin or an analogue thereof.

9. The method of claim 1, wherein said improved pharmaceutic property is improved aerodynamic performance of the particle.

10. The method of claim 1, wherein said improved pharmaceutic property is increased density of the powder.

11. The method of claim 4, wherein said improved pharmaceutic property is improved stability of the active agent of the particle.

12. The method of claim 9, wherein said aerodynamic performance is measured by the percent respirable fraction on a cartridge fill.

13. The method of claim 12, wherein the percent respirable fraction is greater than about 40%.

14. The method of claim 12, wherein the percent respirable fraction is greater than about 50%.

15. The method of claim 12, wherein the percent respirable fraction is greater than about 60%.

16. A dry powder prepared according to the method of claim 1.

17. A method of preparing a dry powder medicament with an improved pharmaceutic property, comprising the steps of:

(a) providing a solution of a diketopiperazine having acidic or basic side chains;

(b) providing a solution of an active agent;

(c) forming particles of the diketopiperazine by adjusting the pH of the solution, resulting in a suspension of particles of the diketopiperazine with acidic or basic side chains in a solvent;

(d) combining the diketopiperazine particles and the active agent solution; and (e) after steps (a)-(d), removing the solvent by spray drying to obtain a dry powder, wherein the dry powder obtained by spray drying has an improved pharmaceutic property as compared to a dry powder obtained by removing solvent by lyophilization, wherein the improved pharmaceutic property is selected from the group consisting of improved stability of the active agent, increased density of the powder, and improved aerodynamic performance of the dry powder.

18. The method of claim 17, wherein said diketopiperazine is a diketopiperazine having the formula 2,5-diketo-3,6-di(4-X-aminobutyl)piperazine, wherein X is selected from the group consisting of succinyl, glutaryl, maleyl, and fumaryl.

19. The method of claim 18, wherein the diketopiperazine is fumaryl diketopiperazine.

20. The method of claim 17, wherein said improved pharmaceutic property is improved stability of the active agent.

21. The method of claim 17, wherein said improved pharmaceutic property is improved aerodynamic performance of the particle.

22. The method of claim 17, wherein said improved pharmaceutic property is increased density of the powder.

23. The method of claim 21, wherein said aerodynamic performance is measured by the percent respirable fraction on a cartridge fill.

24. The method of claim 23, wherein the percent respirable fraction is greater than about 40%.

25. A dry powder prepared according to the method of claim 17.

26. A method for delivering an active agent to a patient in need thereof, comprising administering to the patient an effective amount of the dry powder of claim 16.

27. A method for delivering an active agent to a patient in need thereof, comprising administering to the patient an effective amount of the dry powder of claim 25.

* * * * *